United States Patent
Fitzgerald et al.

(10) Patent No.: US 7,541,034 B1
(45) Date of Patent: Jun. 2, 2009

(54) RECOMBINANT ANTIBODIES AND IMMUNOCONJUGATES TARGETED TO CD-22 BEARING CELLS AND TUMORS

(75) Inventors: David J. Fitzgerald, Rockville, MD (US); Ira Pastan, Potomac, MD (US); Elizabeth Mansfield, Bethesda, MD (US); Robert Kreitman, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/381,497

(22) PCT Filed: Mar. 19, 1998

(86) PCT No.: PCT/US98/05453

§ 371 (c)(1),
(2), (4) Date: Feb. 17, 2000

(87) PCT Pub. No.: WO98/41641

PCT Pub. Date: Sep. 24, 1998

Related U.S. Application Data

(60) Provisional application No. 60/041,437, filed on Mar. 20, 1997.

(51) Int. Cl.
*A61K 39/00* (2006.01)
(52) U.S. Cl. .................. 424/183.1; 530/387.1
(58) Field of Classification Search ............. 530/387.1, 530/387.3, 388.1, 388.8, 388.85, 391.3, 391.9; 435/188, 326, 344.1, 320.1, 325; 536/23.1; 424/130.1, 133.1, 156.1, 178.1
See application file for complete search history.

(56) References Cited

U.S. PATENT DOCUMENTS

| | | | |
|---|---|---|---|
| 4,474,893 A | * | 10/1984 | Reading |
| 4,722,899 A | * | 2/1988 | Hamaoka et al. |
| 4,816,397 A | * | 3/1989 | Boss et al. |
| 4,816,567 A | * | 3/1989 | Cabilly et al. |
| 5,045,451 A | | 9/1991 | Uhr et al. |
| 5,165,923 A | | 11/1992 | Thorpe et al. |
| 5,258,498 A | * | 11/1993 | Huston et al. |
| 5,476,659 A | | 12/1995 | Goodman et al. |
| 5,506,126 A | | 4/1996 | Seed et al. |
| 5,618,920 A | * | 4/1997 | Robinson et al. |

FOREIGN PATENT DOCUMENTS

| | | |
|---|---|---|
| WO | WO94/29350 | 12/1994 |
| WO | WO 95/30004 | * 11/1995 |
| WO | WO 98/41641 | * 9/1998 |

OTHER PUBLICATIONS

Kreitman et al., Cancer Res. 53:819-825, 1993.*
Kuan et al., Biochemistry 35:2872-2877, 1996.*
Reiter et al., Biochemistry 33:5451-5459, 1994.*
Chatterjee et al Cancer Immunol Immunother. 38:75-82, 1994.*
Sevier et al., Clin Chem. 27:1797-1806, 1981.*
Paul, Fundamental immunology, Raven Press, NY, Chapter 8, p. 242, 1993.*
Kreitman et al., Proc. American Assoc. for Cancer REs. 38:28, 1997.*
Amit et al., Science 233:747-753, 1986.*
Rudikoff et al., PNAS 79:1979, 1982.*
Panka et al., PNAS 85:3080-84, 1988.*
Ghetie et al., Cancer Res. 51:5876-80, 1991.*
George et al., Molecular Sequencing ans Synthesis, Selected Methods and Applications Alan R. Liss, inc pp. 127-149, 1988.*
Barton et al., Protein Structure Prediction, A Practical Approach, IRL Press pp. 31-63, 1996.*
Greenspan et al., Nature Biotechnology 7:936-937, 1999.*
Shen et al Int. J. Cancer 42:792-797, 1988.*
Orlandi et al Proc. Natl. Acad. Sci USA 86:3833-37, 1989.*
Ward et al., Nature 341:544-546, 1989.*
Rudikoff et al (Proc Natl Acad Sci USA 1982 vol. 79 p. 1979, 1983.*
Colman (Research in Immunology 145:33-36, 1994.*
J. De Kruif et al.: "Biosynthetically lipid-modified human scFv fragments from phage display libraries as targeting molecules for immunoliposomes." FEBS Letters, vol. 399,, No. 3, Dec. 16, 1996, pp. 232-236, XP002075140 Amsterdam, NL.
D. Luo et al.: "V1-linker-Vh orientation-dependent expression of single chain Fv containing an engineered disulfide-stabilized bond in the framework regions." Journal of Biochemistry, vol. 118, No. 4, Oct. 1, 1995, pp. 825-831, XP002075145 Tokyo, Japan.
E. Mansfield et al.: "Characterization of RFB4-Pseudomonas exotoxin A immunotoxins targeted to CD22 on B-cell malignancies." Bioconjugate Chemistry, vol. 7, No. 5, Sep. 1996, pp. 557-563, XP002075147 Washington, DC, USA.
E. Mansfield et al.: "Recombinant RFB4 immunotoxins exhibit potent cytotoxic activity for CD22-bearing cells and tumors." Blood, vol. 90, No. 5, Sep. 1, 1997, pp. 2020-2026, XP002075148 New York, NY, USA.
V. Rajagopal et al.: "A form of anti-Tac(Fv) which is both single-chain and disulfide-stabilized for imaging CD25+ tumors." Proceedings of the American Association for Cancer Research, vol. 8, Mar. 1997, p. 27 XP002075144 USA see abstract #180.
M. Rodrigues et al.: "Development of a humanized disulfide-stabilized anti-p185HER2 Fv-betalactamase fusion protein for activation of a cephalosporin doxorubicin prodrug." Cancer Research, vol. 55, No. 1, Jan. 1, 1995, pp. 63-70, XP002075146 Baltimore, MD, USA.
Y. Reiter et al., "Engineering antibody Fv fragments for cancer detection and therapy: Disulfide-stabilized Fv fragments," *Nature Biotechnology* (Oct. 1996) 14: 1239-1245.

* cited by examiner

*Primary Examiner*—Larry R. Helms
*Assistant Examiner*—Meera Natarajan
(74) *Attorney, Agent, or Firm*—Townsend and Townsend and Crew LLP

(57) ABSTRACT

Methods and compositions relating to recombinant anti-CD22 antibodies with high binding affinity, and immunoconjugates comprising the anti-CD22 antibody linked to a therapeutic agent such as a *Pseudomonas* exotoxin or a detectable label. The invention provides diagnostic methods, and means to inhibit the growth of malignant B cells.

1 Claim, 12 Drawing Sheets

RFB4 LIGHT CHAIN

```
        D   I   Q   M   T   Q   T   T   S   S   L   S   A   S   L   G   D   R   V   T              20
  1   1 gat atc cag atg acc cag act aca tcc ctg tct gcc tct ctg gga gac aga gtc acc             60

I   S   C   R   A   S   Q   D   I   S   N   Y   L   N   W   Y   Q   Q   K   P              40
 21  61 att agt tgc agg gca agt cag gac att agc aat tat tta aac tgg tat cag cag aaa cca         120

D   G   T   V   K   L   L   I   Y   Y   T   S   I   L   H   S   G   V   P   S              60
 41 121 gat gga act gtt aaa ctc ctg atc tac tac aca tca ata tta cac tca gga gtc cca tca         180

R   F   S   G   S   G   S   G   T   D   Y   S   L   T   I   S   N   L   E   Q              80
 61 181 agg ttc agt ggc agt ggg tct gga aca gat tat tct ctc acc att agc aac ctg gag caa         240

E   D   F   A   T   Y   F   C   Q   Q   G   N   T   L   P   W   T   F   G   G             100
 81 241 gaa gat ttt gcc act tac ttt tgc caa cag ggt aat acg ctt ccg tgg acg ttc ggt gga         300

T   K   L   E   I   K             107
101 301 ggc acc aag ctg gaa atc aaa         121
```

RFB4 HEAVY CHAIN

```
        E   V   Q   L   V   E   S   G   G   G   L   V   K   P   G   G   S   L   K   L              20
  1   1 gaa gtg cag ctg gtg gag tct ggg gga ggc tta gtg aag cct gga ggg tcc ctg aaa ctc          60

S   C   A   A   S   G   F   A   F   S   I   Y   D   M   S   W   V   R   Q   T              40
 21  61 tcc tgt gca gcc tct gga ttc gct ttc agt atc tat gac atg tct tgg gtt cgc cag act         120

P   E   K   R   L   E   W   V   A   Y   I   S   S   G   G   G   T   T   Y   Y              60
 41 121 ccg gag aag agg ctg gag tgg gtc gca tac att agt agt ggt ggt acc acc tac tat             180

P   D   T   V   K   G   R   F   T   I   S   R   D   N   A   K   N   T   L   Y              80
 61 181 cca gac act gtg aag ggc cga ttc acc atc tcc aga gac aat gcc aag aac ctg tac             240

L   Q   M   S   S   L   K   S   E   D   T   A   M   Y   Y   C   A   R   H   S             100
 81 241 ctg caa atg agc agt ctg aag tct gag gac aca gcc atg tat tac tgt gca aga cat agt         300

G   Y   G   S   S   Y   G   V   L   F   A   Y   W   G   Q   G   T   L   V   T             120
101 301 ggc tac ggt agt agc tac ggg gtt ttt gct tac tgg ggc caa ggg act ctg gtc act             360

T   S   A                         123
121 361 gtc tct gca                         369
```

RECOMBINANT ANTIBODIES AND IMMUNOCONJUGATES TARGETED TO CD-22 BEARING CELLS AND TUMORS

The present application is the National Stage of International Application No. PCT/US98/05453, filed Mar. 19, 1998, which claims the priority benefit of U.S. Provisional Application No. 60/041,437, filed Mar. 20, 1997.

TECHNICAL FIELD

The present invention provides anti-CD22 antibodies, anti-CD22 immunoconjugates, CD22 assay methods, and methods of inhibiting the growth of cells expressing CD22.

BACKGROUND OF THE INVENTION

Leukemias and lymphomas are attractive targets for treatment with immunotoxins. The response of patients with B-cell malignancies has been extensively investigated in phase I/II clinical trials of immunotoxin activity. Amlot et al., (1993), *Blood* 82, 2624-2633; Sausville et al., (1995) *Blood* 85, 3457-3465; Grossbard et al., (1993) *Blood* 81, 2263-2271; Grossbard et al., (1993) *Clin. Oncol.* 11, 726-737. To date, some antitumor responses have been noted but immunotoxin mediated toxicity to normal tissue often prevented dose escalations to therapeutic levels. Several B-cell-specific antigens such as CD19, CD22 and CD40 have been targeted by immunotoxins made with plant toxins such as ricin A-chain and bacterial toxins, such as *Pseudomonas* exotoxin A (PE). Uckun et al., (1992), *Blood* 79, 2201-2214; Ghetie et al., (1991), *Cancer Res.* 51, 5876-5880; Francisco et al., (1995), *Cancer Res.* 55, 3099-3104.

CD22, a lineage-restricted B-cell antigen that belongs to the Ig superfamily, is expressed on the surface of many types of malignant B cells, including chronic B-lymphocytic cells (B-CLL), B lymphoma cells such as Burkitt's lymphomas, and hairy cell leukemias, as well as on normal mature B lymphocytes. CD22 is not present on the cell surface in early stages of B-cell development, and is not expressed on stem cells. Vaickus et al., (1991), *Crit. Rev. Oncol/Hematol.* 11, 267-297. Additionally, no shed antigen can be detected in normal human serum or serum from patients with CLL. Li et al., (1989), *Cell. Immunol.* 118, 85-99.

RFB4 IgG is an anti-CD22 monoclonal antibody. This antibody has been chemically conjugated to both ricin and *Pseudomonas* exotoxin A (PE) and has shown activity against B-cells both in vitro and in vivo; Ghetie et al., (1991), *Cancer Res.* 51, 5876-5880; Ghetie et al., (1988), *Cancer Res.* 48, 2610-2617. RFB4 is highly specific for cells of the B lineage and has no detectable cross-reactivity with any other normal cell type. Li et al., (1989), *Cell. immunol.* 118, 85-99. RFB4 IgG has previously been covalently coupled to both ricin A-chain and a truncated form of PE called PE35. These conjugate molecules were effective against experimental lymphoma xenograft models, and in the clinical setting, the ricin-based immunotoxin also has shown some efficacy against human disease. Amlot et al., (1993), *Blood* 82, 2624-2633; Sausville, (1995), *Blood* 85, 3457-3465.

While chemical conjugates are frequently very stable and potent, they are large and presumably heterogeneous at their linkage sites, which may result in sub-optimal activity. The requirements for making large quantities of IgG and chemical conjugation also put some limitations on the ability to manufacture the drug. Because the ability to penetrate tumors is inversely related to the size of the penetrating molecule, the large size of antibody-toxin conjugates may impair their ability to penetrate tumor masses such as those found in lymphomas.

SUMMARY OF THE INVENTION

In one aspect, the present invention relates to recombinant immunoconjugates and the antibody components that are surprisingly very stable and potent against cells bearing the CD22 antigen, most typically malignant B cells. The immunoconjugate comprises a therapeutic agent or a detectable label peptide bonded to a recombinant anti-CD22 antibody disulfide stabilized through a cysteine placed at amino acid position 44 of the $V_H$ and a cysteine at amino acid position 100 of the $V_L$. The therapeutic agent can be a toxin such as a *Pseudomonas* exotoxin (PE) or a cytotoxic fragment thereof (e.g., PE38). In some embodiments, the anti-CD22 antibody is an RFB4 binding fragment. In other embodiments, the antibody comprises a variable heavy ($V_H$) chain substantially similar to SEQ ID NO:2, encoded by SEQ ID NO:1 and a variable light ($V_L$) chain substantially similar to SEQ ID NO:4, encoded by SEQ ID NO:3. (See also FIG. 1.) The variable heavy chain can be peptide bonded to the amino terminus of the toxin. Optionally, the $V_H$ chain is peptide bonded to the $V_L$ chain through a linker peptide such as the linker peptide of SEQ ID NO:5. In some embodiments, the $V_H$ chain is linked to the $V_L$ chain through a cysteine-cysteine disulfide bond.

In another aspect, the present invention relates to an expression cassette encoding the recombinant immunoconjugate and to a host cell comprising an expression cassette encoding the recombinant immunoconjugates. In some embodiments the anti-CD22 antibody comprises a variable heavy ($V_H$) chain substantially similar to SEQ ID NO:2 and a variable light ($V_L$) chain substantially similar to SEQ ID NO:4.

In yet another aspect, the present invention relates to a method for inhibiting the growth of a malignant B-cell. The method comprises the steps of contacting the malignant B-cell with an effective amount of a recombinant immunoconjugate comprising a toxin peptide bonded to an anti-CD22 antibody. The toxin can be a *Pseudomonas* exotoxin (PE) or a cytotoxic fragment thereof such as PE38. In some embodiments, the malignant B-cell is contacted with the immunoconjugate in vivo. The malignant B-cell can be a rodent B-cell, a canine B-cell, or a primate B-cell (e.g., human B-cell).

In another aspect, the present invention relates to an anti-CD22 Fv fragment comprising a variable heavy ($V_H$) chain substantially similar to SEQ ID NO:2 and a variable light ($V_L$) chain substantially similar to SEQ ID NO:4. The Fv fragment can be a dsFv fragment. In some embodiments the Fv fragment is detectably labeled, in others the Fv fragment is conjugated to a therapeutic agent. The therapeutic agent can be a *Pseudomonas* exotoxin (PE) or cytotoxic fragment thereof.

In a further aspect, the present invention is directed to a method for detecting the presence of CD22 protein in a biological sample. The method comprises the step of contacting the biological sample with an anti-CD22 antibody comprising a variable heavy ($V_H$) chain substantially similar to SEQ ID NO:2 and a variable light ($V_L$) chain substantially similar to SEQ ID NO:4, and allowing the antibody to bind to the CD22 protein under immunologically reactive conditions, wherein detection of the bound antibody indicates the presence of the CD22 protein. In some embodiments the antibody is a dsFv fragment. The antibody employed in the method can be detectably labeled. In some embodiments, the method is performed in vivo in a mammal.

BRIEF DESCRIPTION OF THE DRAWINGS

FIG. 1: Deduced amino acid sequence of the variable region of RFB4 light (SEQ ID NO:4; nucleotides=SEQ ID NO:31) and heavy (SEQ ID NO:2; nucleotides=SEQ ID NO:1) chains. Amino acids shown in bold were determined by N-terminal protein sequence analysis.

Nude female mice were irradiated (3 Gy) on day −3 and on day 0 they were injected subcutaneously with 10$^7$ CA46 cells. Tumors formed by day 4, and the mice were treated every other day for 3 doses of the indicated toxins and doses. Responses were dose dependent and not obtained with the negative control molecules anti-Tac(Fv)-PE38 and RFB4-IgG.

Figures 9A, 9B:
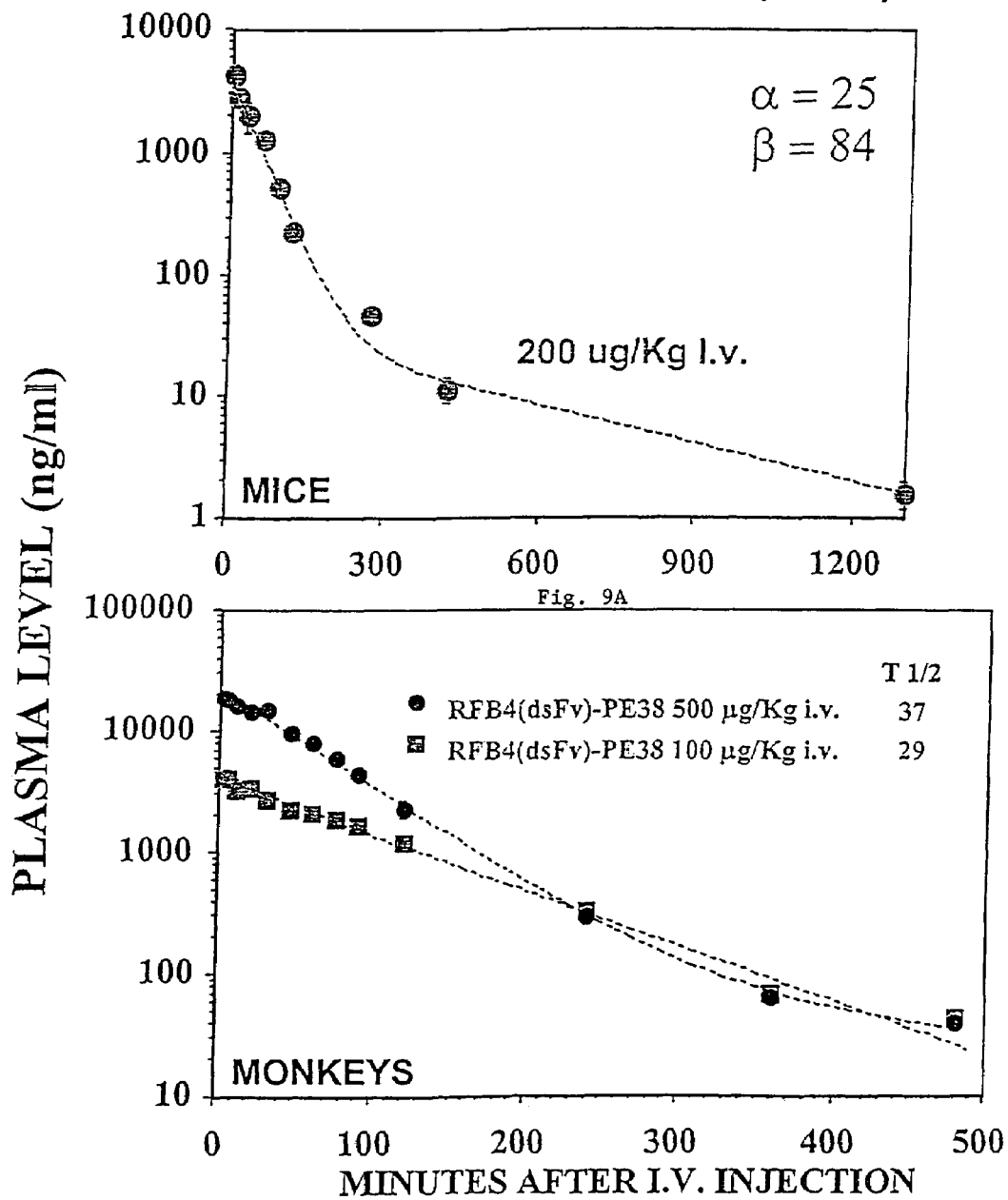

FIGS. 9A and 9B: Pharmacokinetics of RFB4(dsFv)-PE38. Mice in groups of 3 were injected with RFB4(dsFv)-PE38. Blood was drawn at the indicated time points. Two Cynomolgus monkeys were treated, each at the indicated dose. Plasma levels were determined by a cytotoxicity assay.

DETAILED DESCRIPTION OF THE INVENTION

Overview

The present invention provides recombinant antibodies and immunoconjugates that are highly specific for CD22. An exemplary molecule employed a *Pseudomonas* exotoxin (PE) genetically fused to an anti-CD22 disulfide stabilized antibody, preferably a Fv (dsFV) fragment. Quite unexpectedly, the recombinant PE-dsFv immunotoxin proved nearly 10-fold more cytotoxic than the single chain Fv (scFv) fragment. The dsFv was produced by mutating the nucleic acids at amino acid position 44 of the $V_H$ and the amino acid position 100 of the $V_L$ to encode for a cysteine.

Many of the recombinant molecules produced from constructs of the present invention are one-third the size of IgG-toxin chemical conjugates and are homogeneous in composition. Small size will improve drug penetration in solid tumors, while elimination of the constant portion of the IgG molecule results in faster clearance from the circulation of experimental animals and patients. Together, these properties will lessen side effects by reducing the time in which the immunotoxin (IT) can interact with non-target tissues and tissues that express very low levels of antigen. And, homogeneous preparations of recombinant immunotoxins can easily be produced in large quantities.

The surprisingly higher activity and the unique pharmacological properties afforded by the anti-CD22 disulfide stabilized immunoconjugates of the present invention make them highly effective therapeutic agents for treatment of B-cell malignancies or for detection agents of such malignancies.

DEFINITIONS

Units, prefixes, and symbols can be denoted in their SI accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention which can be had by reference to the specification as a whole. Accordingly, the terms defined immediately below are more fully defined by reference to the specification in its entirety.

The term "CD22" includes reference to a CD22 antigen present on the surface of B-cells of a mammal such as rats, mice, and primates, particularly humans. See, e.g., Wilson et al., J. Exp. Med. 173(1):137-146 (1991); Wilson et al., J. Immunol, 150(11):5013-5024 (1993), each of which is incorporated herein by reference. The term "CD22 protein" includes reference to both CD22 and RFB4 immunoreactive fragments of CD22. Such CD22 immunoreactive fragments have an affinity to an RFB4 binding fragment (See, e.g., Example 1) at least 5-fold greater than a non-CD22 control protein. An exemplary assay for binding affinity is described in Example 2.

The term "cytotoxic fragment" with respect to *Pseudomonas* exotoxin (PE) includes reference to a contiguous subsequence from native PE, or native PE which lacks one or more contiguous subsequences present in the native molecule, or is a conservatively modified variant of such fragments. The cytotoxic fragment retains at least 50%, preferably 75%, more preferably at least 90%, and most preferably 95% of the cytotoxicity of native PE. The native PE sequence is published. Exemplary cytotoxic PE fragments of PE35, PE38, and PE40 are disclosed in U.S. Pat. Nos. 5,602,095; 5,608,039; and 4,892,827, each of which is incorporated herein by reference.

"Biological sample" as used herein is a sample of biological tissue or fluid that contains CD22 or a CD22 protein. Such samples include, but are not limited to, sputum, amniotic fluid, blood, blood cells (e.g., white cells), or tissue. Biological samples may also include sections of tissues such as frozen sections taken for histological purposes. Examples of biological samples include a cell sample from the immune system (e.g., B cells). A biological sample is typically obtained from a multicellular eukaryote, preferably a mammal such as rat, mice, cow, dog, guinea pig, or rabbit, and most preferably a primate such as macaques, chimpanzees, or humans.

As used herein, "recombinant" includes reference to a protein produced using cells that do not have in their native form an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell or express native genes that are otherwise abnormally expressed, under expressed or not expressed at all.

The term "therapeutic agent" includes any number of peptide compounds currently known or later developed to act as anti-inflammatories, cytokines, anti-infectives, enzyme activators or inhibitors, allosteric modifiers, or antibiotics or those having other therapeutic effects.

The terms "effective amount" or "amount effective to" or "therapeutically effective amount" includes reference to a dosage sufficient to produce a desired result, such as inhibiting cell protein synthesis by at least 50%, or killing the cell.

The term "in vivo" includes reference to inside the body of the organism from which the cell was obtained. "Ex vivo" means outside the body of the organism from which the cell was obtained.

The term "immunoconjugate" includes reference to a covalent linkage of a therapeutic agent or a detectable label to an antibody such as an antibody binding fragment. The linkage can be direct or indirect through a linker peptide.

The term "label" or "detectable label" includes reference to any composition detectable by spectroscopic, photochemical, biochemical, immunochemical, electrical, optical or chemical means.

The term "toxin" includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE and the B chain of DT) and replacing it with a different antibody targeting moiety.

As used herein, "mammalian cells" includes reference to cells derived from mammals including humans, rats, mice, guinea pigs, chimpanzees, or macaques. The cells may be cultured in vivo or ex vivo.

As used herein, "expressed" includes reference to translation of a nucleic acid into a protein.

As used herein, "nucleic acid" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.*, 82:2306-2309 (1985), or the ciliate *Macronucleus*, may be used when the nucleic acid is expressed in using the translational machinery of these organisms.

As used herein, "antibody" includes reference to an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies) and recombinant single chain Fv fragments (scFv) or disulfide stabilized (dsFv) Fv fragments (See, U.S. Ser. No. 08/077,252, incorporated herein by reference), which is incorporated herein by reference. The term "antibody" also includes antigen binding forms of antibodies (e.g., Fab', F(ab')$_2$, Fab, Fv, rIgG, and inverted IgG). See also, Pierce Catalog and Handbook, 1994-1995 (Pierce Chemical Co., Rockford, Ill.). An antibody immunologically reactive with a particular antigen can be generated in vivo or by recombinant methods such as selection of libraries of recombinant antibodies in phage or similar vectors. See, e.g., Huse et al. (1989) *Science* 246:1275-1281; and Ward, et al. (1989) *Nature* 341:544-546; and Vaughan et al. (1996) *Nature Biotechnology*, 14:309-314.

The term "binding fragment" with respect to an antibody refers to an antibody which lacks substantially all of the Fc region of an in vivo generated antibody. Exemplary antibody binding fragments include scFv, dsFv, Fab, and (Fab')$_2$ fragments.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow and Lane (1988) *Antibodies, A Laboratory Manual*, Cold Spring Harbor Publications, New York, for a description of immunoassay formats and conditions.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are sometimes described by shorthand designations as follows:

| Amino Acid Nomenclature | | |
|---|---|---|
| Name | 3-letter | 1-letter |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

The terms "substantially similar" in the context of a peptide indicates that a peptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

In turn, "sequence identity" in the context of two nucleic acid or polypeptide sequences includes reference to the nucleotides (or residues) in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11-17 (1988) e.g., as implemented in the program PC/GENE (intelligenetics, Mountain View, Calif., USA). An indication that two peptide sequences are substantially similar is that one peptide is immunologically reactive with antibodies raised against the second peptide. Thus, a peptide is substantially similar to a second peptide, for example, where the two peptides differ only by a conservative substitution.

Nucleic acid sequences are "substantially similar" if they encode substantially similar peptides.

A "comparison window", as used herein, includes reference to a segment of about 10-20 residues in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman (1981) *Adv. Appl. Math.* 2: 482; by the homology alignment algorithm of Needleman and Wunsch (1970) *J. Mol. Biol.* 48: 443; by the search for similarity method of Pearson and Lipman (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene,* 73: 237-244 and Higgins and Sharp (1989) *CABIOS* 5: 151-153; Corpet, et al. (1988) *Nucleic Acids Research* 16, 10881-90; Huang, et al. (1992) *Computer Applications in the Biosciences* 8, 155-65, and Pearson, et al. (1994) *Methods in Molecular Biology* 24, 307-31.

The term "contacting" includes reference to placement in direct physical association.

The term "malignant B-cell" includes reference to transformed B-cells such as, but not limited to, chronic B-lymphocytic cells (B-CLL), B lymphoma cells such as Burkitt's lymphomas, and hairy cell leukemias, as well as on normal mature B lymphocytes. The B-cells are mammalian B-cells, such as rats, mice, and primates, particularly human B-cells. Malignant B-cells express CD22, in whole or part, on their surface such that anti-CD22 antibodies recognize and bind to malignant B-cells at least 5 times greater, and more preferably at least 10 times greater binding affinity, than a B-cell not bearing CD22 using a standard binding assay. An exemplary binding assay is described herein in Example 2.

The term "expression vector" includes reference to a nucleic acid construct, generated recombinantly or synthetically, with a series of specified nucleic acid elements which permit transcription of a particular nucleic acid in a host cell. The expression vector can be part of a plasmid, virus, or nucleic acid fragment. Typically, the expression vector includes a nucleic acid to be transcribed, and a promoter.

The term "linker peptide" includes reference to a peptide within an antibody binding fragment (e.g., Fv fragment) which serves to indirectly bond the variable heavy chain to the variable light chain.

By "host cell" is meant a cell which can support the replication or expression of the expression vector. Host cells may be prokaryotic cells such as *E. coli,* or eukaryotic cells such as yeast, insect, amphibian, or mammalian cells.

As used herein, the term "anti-CD22" in reference to an antibody or an Fv fragment which is specific for CD22, includes reference to an antibody which is generated to CD22, particularly an extracellular epitope of CD22. In preferred embodiments, the CD22 is a primate CD22 such as human CD22. Sources of CD22 are well known.

The term "RFB4 binding fragment" includes reference to an antibody which binds to the same epitope as an RFB4 dsFv and has at least 70%, more preferably at least 80%, and most preferably at least 90% of the binding affinity of RFB4 dsFv fragment as disclosed herein at, e.g., Example 1. An exemplary assay for binding affinity is described in Example 2.

A. Conservatively Modified Variants of PE

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level.

The term "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

B. Assaying for Cytotoxicity of PE

*Pseudomonas* exotoxins employed in the invention can be assayed for the desired level of cytotoxicity by assays well known to those of skill in the art. Exemplary toxicity assays are described herein at, e.g., Example 4. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE.

Anti-CD22 Antibodies

The present invention provides antibodies targeted to extracellular determinants of CD22. CD22 is an antigen present on B-cells. The immunoconjugates disclosed herein are targeted to CD22 using antibodies of the present invention. These antibodies are selectively reactive under immunological conditions to those determinants of CD22 displayed on the surface of B-cells and accessible to the antibody from the extracellular milieu. In preferred embodiments the antibody employed in immunoconjugate compositions is an RFB4 binding fragment.

The term "selectively reactive" or "specific to" includes reference to the preferential association of an antibody, in whole or part, with a cell or tissue bearing the CD22 target molecule and not to cells or tissues lacking that target molecule. It is, of course, recognized that a certain degree of non-specific interaction may occur between a molecule and a non-target cell or tissue. Nevertheless, specific binding, may be distinguished as mediated through specific recognition of the target CD22 molecule. Typically specific binding results in a much stronger association between the delivered molecule and cells bearing CD22 than between the bound molecule and cells lacking CD22. Specific binding typically results in greater than 2 fold, preferably greater than 5 fold, more preferably greater than 10 fold and most preferably greater than 100 fold increase in amount of bound ligand (per unit time) to a cell or tissue bearing CD22 as compared to a cell or tissue lacking CD22. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

Preferably, immunologically reactive conditions employed in the methods of the present invention are "physiological conditions" which includes reference to conditions (e.g., temperature, osmolarity, pH) that are typical inside a living mammal or a mammalian cell. While it is recognized that some organs are subject to extreme conditions, the intra-organismal and intra-cellular environment normally varies around pH 7 (i.e. from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The anti-CD22 antibody employed in the present invention can be linked to *Pseudomonas* exotoxin (PE) through the PE amino terminus, through an interior amino acid residue of PE such as cysteine, or any combination thereof. Similarly, PE can be linked directly to the heavy, light, or Fc region of the antibody. Linkage can occur through the antibody's amino or carboxy termini, or through an interior amino acid residue. Further, multiple PE molecules (e.g., any one of from 2-10) can be linked to the anti-CD22 antibody and/or multiple antibodies (e.g., any one of from 2-5) can be linked to a PE molecule. The antibodies used in a multivalent immunoconjugate composition of the present invention can be to the same or different CD22 epitope.

In preferred embodiments of the present invention, the anti-CD22 antibody is an antibody binding fragment such as an scFv or dsFv antibody such as an RFB4 dsFv. Fv fragments are typically about 25 kDa for and contain a complete antigen-binding site. The $V_H$ and $V_L$ chains of the Fv fragments are held together by noncovalent interactions. These chains tend to dissociate upon dilution, so methods have been developed to crosslink the chains through glutaraldehyde, intermolecular disulfides, or a peptide linker. In some preferred embodiments, the Fv antibody binding fragment has an RFB4 variable heavy chain substantially similar to SEQ ID NO:2 or a conservatively modified variant thereof, and/or a RFB4 variable light chain substantially similar to SEQ ID NO:4 or conservatively modified variant thereof. Such conservative variants employed in dsFV fragments will retain cysteine residues used for disulfide linkages between the chains. Conservatively modified variants of the prototype sequence of SEQ ID NO:2 and/or the prototype sequence of SEQ ID NO:4 have at least 80% sequence similarity, preferably at least 85% sequence similarity, more preferably at least 90% sequence similarity, and most preferably at least 95% sequence similarity at the amino acid level to its prototype sequence.

In some embodiments of the present invention, the antibody binding fragments are directly linked to PE through the light chain. And in some embodiments, antibody binding fragments are directly linked to PE through the heavy chain. The Fv fragments can be linked to PE via their amino or carboxyl termini. In preferred embodiments, the PE is PE38.

The variable heavy and light chains ($V_H$ and $V_L$) of disulfide stabilized Fv fragments are covalently linked via a disulfide linkage between cysteine residues present in each of the two chains. A disulfide stabilized Fv (dsFv) fragment is one in which the native Fv sequence has been mutated at a specific position to yield a cysteine residue that will provide an additional disulfide bond when the resulting antibody molecule is formed. The pair of amino acids to be selected are, in order of decreasing preference:

$V_H 44$-$V_L 100$,
$V_H 105$-$V_L 43$,
$V_H 105$-$V_L 42$,
$V_H 44$-$V_L 101$,
$V_H 106$-$V_L 43$,
$V_H 104$-$V_L 43$,
$V_H 44$-$V_L 99$,
$V_H 45$-$V_L 98$,
$V_H 46$-$V_L 98$,
$V_H 103$-$V_L 43$,
$V_H 103$-$V_L 44$,
$V_H 103$-$V_L 45$.

Most preferably, substitutions of cysteine are made at the positions:

$V_H 44$-$V_L 100$; or
$V_H 105$-$V_L 43$.

(The notation $V_H 44$-$V_L 100$, for example, refers to a polypeptide with a $V_H$ having a cysteine at position 44 and a cysteine in $V_L$ at position 100; the positions being in accordance with the numbering given in "Sequences of Proteins of Immunological Interest," E. Kabat, et al., U.S. Government Printing Office, NIH Publication No. 91-3242 (1991); which is incorporated herein by reference ("Kabat and Wu"). $V_H$ and $V_L$ are identified as known in the art, including Kabat and Wu. Amino acid positions of $V_H$ or $V_L$ herein are with reference to Kabat and Wu. DsFv fragments comprise at least one disulfide linkage but may comprise 2, 3, 4, 5 or more linkages as desired.

While the two $V_H$ and $V_L$ chains of some antibody embodiments can be directly joined together, one of skill will appreciate that the molecules may be separated by a peptide linker consisting of one or more amino acids. Generally the peptide linker will have no specific biological activity other than to join the proteins or to preserve some minimum distance or other spatial relationship between them. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, preferably no more than 30 amino acids, and more preferably no more than 20 amino acids in length. In some embodiments, the peptide linker is a concatamer of the sequence Gly-Gly-Gly-Ser (SEQ ID NO:5), preferably 2, 3, 4, 5, or 6 such sequences. Peptide linkers and their use are well-known in the art. See, e.g., Huston et al., *Proc. Natl. Acad. Sci. USA*, supra; Bird et al., *Science*, supra; Glockshuber et al., supra; U.S. Pat. No. 4,946,778, U.S. Pat. No. 5,132,405 and most recently in Stemmer et al., *Biotechniques* 14:256-265 (1993), all incorporated herein by reference.

Recombinant Antibody Production

The antibody is a recombinant one, typically an scFv or dsFv. Methods of making Fv antibodies have been described. See, Huse et al. *Science* 246: 1275-1281 (1989); and Ward, et al. *Nature* 341: 544-546 (1989); and Vaughan et al. (1996) *Nature Biotechnology*, 14:309-314. In general suitable antibodies will usually bind with an affinity constant of at least $10^{-7}$ M, preferably at least $10^{-8}$ M, preferably at least $10^{-9}$ M, more preferably at least $10^{-10}$ M, most preferably at least $10^{-11}$ M.

Binding Affinity of Antibodies

The antibodies of this invention are capable of specifically binding an extracellular epitope of CD22. An anti-CD22 antibody has binding affinity for CD22 if the antibody binds or is capable of binding CD22 as measured or determined by standard antibody-antigen assays, for example, competitive assays, saturation assays, or standard immunoassays such as ELISA or RIA. This definition of specificity applies to single heavy and/or light chains, CDRs, fusion proteins or fragments of heavy and/or light chains, that are specific for CD22 if they bind CD22 alone or in combination.

In competition assays the ability of an antibody to bind a ligand is determined by detecting the ability of the antibody to compete with the binding of a compound known to bind the ligand. Numerous types of competitive assays are known and are discussed herein. Alternatively, assays that measure binding of a test compound in the absence of an inhibitor may also be used. For instance, the ability of a molecule or other compound to bind CD22 can be detected by labelling the molecule of interest directly or the molecule be unlabelled and detected indirectly using various sandwich assay formats. Numerous types of binding assays such as competitive binding assays are known (see, e.g., U.S. Pat. Nos. 3,376,110, 4,016,043, and Harlow and Lane, *Antibodies: A Laboratory Manual*, Cold Spring Harbor Publications, N.Y. (1988), which are incorporated herein by reference). Assays for measuring binding of a test compound to one component alone rather than using a competition assay are also available. For instance, antibodies can be used to identify the presence of the ligand. Standard procedures for monoclonal antibody assays, such as ELISA, may be used (see, Harlow and Lane, supra). For a review of various signal producing systems which may be used, see, U.S. Pat. No. 4,391,904, which is incorporated herein by reference.

Production of Immunoconjugates

A. Immunotoxins

Toxins can be employed with antibodies of the present invention to yield immunotoxins. Exemplary toxins include ricin, abrin, diphtheria toxin and subunits thereof, as well as botulinum toxins A through F. These toxins are readily available from commercial sources (e.g, Sigma Chemical Company, St. Louis, Mo.). *Diptheria* toxin is isolated from *Corynebacterium diphtheriae*. Ricin is the lectin RCA60 from *Ricinus communes* (Castor bean). The term also references toxic variants thereof. See, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65,000 and 120,000, respectively. Nicholson and Blaustein, *J. Biochim. Biophys. Acta,* 266:543 (1972). The A chain is responsible for inactivating protein synthesis and killing cells. The B chain binds ricin to cell-surface galactose residues and facilitates transport of the A chain into the cytosol (Olsnes et al., *Nature,* 1974; 249:627-631). See, U.S. Pat. No. 3,060,165.

Abrin includes toxic lectins from *Abrus precatorius*. The toxic principles, abrin a, b, c, and d, have a molecular weight of from about 63,000 and 67,000 Da and are composed of two disulfide-linked polypeptide chains A and B. The A chain inhibits protein synthesis; the B-chain (abrin-b) binds to D-galactose residues. See, Funatsu et al., The amino acid sequence of the A-chain of abrin-a and comparison with ricin, *Agr. Biol. Chem.* 52:1095 (1988). See also, Olsnes, *Methods Enzymol.* 50:330-335 (1978).

In preferred embodiments, the toxin is *Pseudomonas* exotoxin. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al., *J. Biol. Chem.* 264: 14256-14261 (1989), incorporated by reference herein.

The *Pseudomonas* exotoxins (PE) employed in the present invention include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or pre-protein). Cytotoxic fragments of PE include PE40, PE38, and PE35. PE40 is a truncated derivative of PE as previously described in the art. See, Pai et al., Proc. Natl. Acad. Sci. USA, 88:3358-62 (1991); Kondo et al., J. Biol. Chem. 263:9470-9475 (1988). PE38 is a truncated PE composed of amino acids 253-364 and 381-613. PE35 is a 35 kD carboxyl-terminal fragment of PE composed of a Met at position 280 followed by amino acids 281-364 and 381-613 of native PE. In preferred embodiments, the cytotoxic fragment PE38 is employed. PE38 is a pro-protein which can be activated to its cytotoxic form upon processing within a cell.

With the *Pseudomonas* exotoxins and antibodies herein provided, one of skill can readily construct a variety of clones containing functionally equivalent nucleic acids, such as nucleic acids which differ in sequence but which encode the same PE or antibody sequence. Thus, the present invention provides nucleic acids encoding antibodies and conjugates and fusions thereof.

B. Recombinant Methods

The nucleic acids of the present invention can be prepared by any suitable method including, for example, cloning and restriction of appropriate sequences or by direct chemical synthesis by methods such as the phosphotriester method of Narang et al. *Meth. Enzymol.* 68: 90-99 (1979); the phosphodiester method of Brown et al., *Meth. Enzymol.* 68:109-151 (1979); the diethylphosphoramidite method of Beaucage et al., *Tetra. Lett.,* 22: 1859-1862 (1981); the solid phase phosphoramidite triester method described by Beaucage and Caruthers (1981), *Tetrahedron Letts.,* 22(20):1859-1862, e.g., using an automated synthesizer, e.g., as described in Needham-VanDevanter et al. (1984) *Nucleic Acids Res.,* 12:6159-6168; and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences. Cloning methodologies to accomplish these ends, and sequencing methods to verify the sequence of nucleic acids are well known in the art and exemplified herein.

The immunoconjugates, PE, and antibodies of the present invention can also be constructed in whole or in part using standard peptide synthetic methods. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, *Solid-Phase Peptide Synthesis*; pp. 3-284 in *The Peptides: Analysis, Synthesis, Biology. Vol.* 2: *Special Methods in Peptide Synthesis, Part A.,* Merrifield, et al. *J. Am. Chem. Soc.,* 85: 2149-2156 (1963), and Stewart et al., *Solid Phase Peptide Synthesis, 2nd ed.* Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicyclohexylcarbodiimide) is known to those of skill.

Other examples of appropriate cloning and sequencing techniques, and instructions sufficient to direct persons of skill through many cloning exercises are found in Sambrook, et al., *Molecular Cloning: A Laboratory Manual* (2nd Ed., Vols. 1-3, Cold Spring Harbor Laboratory (1989)), *Methods in Enzymology*, Vol. 152: *Guide to Molecular Cloning Techniques* (Berger and Kimmel (eds.), San Diego: Academic Press, Inc. (1987)), or *Current Protocols in Molecular Biology*, (Ausubel, et al. (eds.), Greene Publishing and Wiley-Interscience, New York (1987). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding native PE or anti-CD22 antibodies can be modified to form the PE, antibodies, or immunoconjugates of the present invention. Modification by site-directed mutagenesis is well known in the art. Nucleic acids encoding native PE or anti-CD22 antibodies (e.g., RBF4) can be amplified by in vitro methods. Amplification methods include the polymerase chain reaction (PCR), the ligase chain reaction (LCR), the transcription-based amplification system (TAS), the self-sustained sequence replication system (SSR). A wide variety of cloning methods, host cells, and in vitro amplification methodologies are well-known to persons of skill.

Once the nucleic acids encoding a PE, anti-CD22 antibody, or immunoconjugate of the present invention is isolated and cloned, one may express the desired protein in a recombinantly engineered cell such as bacteria, yeast, insect and mammalian cells. It is expected that those of skill in the art are knowledgeable in the numerous expression systems available for expression of proteins including *E. coli*, other bacterial hosts, yeast, and various higher eukaryotic cells such as the COS, CHO and HeLa cells lines and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the protein. To obtain high level expression of a cloned gene, it is desirable to construct expression vectors which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eucaryotic cells, the control sequences can include a promoter and preferably an enhancer derived from immunoglobulin genes, SV40, cytomegalovirus, and a polyadenylation sequence, and may include splice donor and acceptor sequences. The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

One of skill would recognize that modifications can be made to a nucleic acid encoding a polypeptide of the present invention (i.e., anti-CD22 antibody, PE, or immunoconjugate formed from their combination) without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

C. Purification

Once expressed, the recombinant immunoconjugates, antibodies, and/or *Pseudomonas* exotoxins of the present invention can be purified according to standard procedures of the art, including ammonium sulfate precipitation, affinity columns, column chromatography, and the like (see, generally, R. Scopes, *Protein Purification*, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, the polypeptides should be substantially free of endotoxin for pharmaceutical purposes and may then be used therapeutically.

Methods for expressing of single chain antibodies and/or refolding to an appropriate folded form, including single chain antibodies, from bacteria such as *E. coli* have been described and are well-known and are applicable to the antibodies of this invention. See, Buchner et al., *Analytical Biochemistry* 205:263-270 (1992); Pluckthun, *Biotechnology,* 9:545 (1991); Huse, et al., *Science,* 246:1275 (1989) and Ward, et al., *Nature,* 341:544 (1989), all incorporated by reference herein.

Often, functional protein from *E. coli* or other bacteria is generated from inclusion bodies and requires the solubilization of the protein using strong denaturants, and subsequent refolding. In the solubilization step, a reducing agent must be present to dissolve disulfide bonds as is well-known in the art. An exemplary buffer with a reducing agent is: 0.1 M Tris, pH8, 6M guanidine, 2 mM EDTA, 0.3 M DTE (dithioerythritol). Reoxidation of protein disulfide bonds can be effectively catalyzed in the presence of low molecular weight thiol reagents in reduced and oxidized form, as described in Saxena et al., *Biochemistry* 9: 5015-5021 (1970), incorporated by reference herein, and especially described by Buchner, et al., *Anal. Biochem.*, supra (1992).

Renaturation is typically accomplished by dilution (e.g. 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a necessary modification to the single chain antibody protocol, the heavy and light chain regions were separately solubilized and reduced and then combined in the refolding solution. A preferred yield is obtained when these two proteins are mixed in a molar ratio such that a molar excess of one protein over the other does not exceed a 5 fold excess. It is desirable to add excess oxidized glutathione or other oxidizing low molecular weight compounds to the refolding solution after the redox-shuffling is completed.

Pharmaceutical Compositions and Administration

The antibody and/or immunoconjugate compositions of this invention (i.e., PE linked to an antibody), are particularly useful for parenteral administration, such as intravenous administration or administration into a body cavity or lumen of an organ. The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunoconjugate composition for intravenous administration would be at a total treatment of about 0.3 to about 30 mg/kg per day, with the dosage preferably administered continuously or allocated at a dosage of about 0.1 to 10 mg/kg three times per day. Preferably, the dosage would be given every other day at about 0.2 to 2 mg/kg three times a day or 0.6 to 6 mg/kg per day in a continuous infusion. Actual methods for preparing administrable compositions will be known or apparent to those skilled in the art and are described in more detail in such publications as *Remington's Pharmaceutical Science*, 19th ed., Mack Publishing Company, Easton, Pa. (1995).

The composition including the present invention's immunoconjugate can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient. Preferably, the dosage is administered three times a day every other day or continuously every other day but may be applied periodically until either a therapeutic result is achieved or until side effects warrant discontinuation of therapy. Generally, the dose should be sufficient to treat or ameliorate symptoms or signs of disease without producing unacceptable toxicity to the patient. An effective amount of the compound is that which provides either subjective relief of a symptom(s) or an objectively identifiable improvement as noted by the clinician or other qualified observer.

Controlled release parenteral formulations of the immunoconjugate compositions of the present invention can be made as implants, oily injections, or as particulate systems. For a broad overview of protein delivery systems see, Banga, A. J., "Therapeutic Peptides and Proteins: Formulation, Processing, and Delivery Systems" Technomic Publishing Company, Inc. 1995. Lancaster, Pa., incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, e.g., Kreuter, J. 1994. "Nanoparticles," in *Colloidal Drug Delivery Systems*, J. Kreuter, ed., Marcel Dekker, Inc., New York, N.Y., pp. 219-342; Tice and Tabibi. 1992. "Parenteral Drug Delivery: Injectibles," in *Treatise on Controlled Drug Delivery*, A. Kydonieus, ed., Marcel Dekker, Inc. New York, N.Y., pp. 315-339, both of which are incorporated herein by reference.

Polymers can be used for use ion controlled release of immunoconjugate compositions of the present invention. Various degradable and nondegradable polymeric matrices for use in controlled drug delivery are known in the art. Langer, R. 1993. "Polymer-Controlled Drug Delivery Systems," *Accounts Chem. Res.*, 26:537-542. For example, the block copolymer, polaxamer 407 exists as a mobile viscous at low temperatures but forms a semisolid gel at body temperature. It has shown to be an efficacious vehicle for formulation and sustained delivery of recombinant interleukin-2 and urease. Johnston et al., *Pharm. Res.*, 9:425-434 (1992); Pec et al., *J. Parent. Sci. Tech.*, 44(2):58-65 (1990). Hydroxyapatite can also be used as a microcarrier for controlled release of proteins. Ijntema et al., *Int. J. Pharm.*, 112:215-224 (1994). Liposomes can be used for controlled release as well as drug targeting of entrapped drug. Betageri et al. 1993. "Targeting of Liposomes," in *Liposome Drug Delivery Systems*, Technomic Publishing Co., Inc., Lancaster, Pa. Numerous additional systems for controlled delivery of therapeutic proteins are known. See, e.g., U.S. Pat. Nos. 5,055,303, 5,188,837, 4,235,871, 4,501,728, 4,837,028, 4,957,735 and 5,019,369; 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the recombinant fusion proteins of the present invention are included a variety of disease conditions caused by specific human cells that may be eliminated by the toxic action of the protein. One preferred application for the immunoconjugates of the invention is the treatment of malignant B cells expressing CD22. Exemplary malignant B cells include chronic B-lymphocytic cells (B-CLL), B lymphoma cells such as Burkitt's lymphomas, and hairy cell leukemias.

Diagnostic Kits

In another embodiment, this invention provides for kits for the detection of CD22 or an immunoreactive fragment thereof, (i.e., collectively, a "CD22 protein") in a biological sample. Kits will typically comprise an anti-CD22 antibody of the present invention comprising a variable heavy ($V_H$) chain substantially similar to SEQ ID NO:2 and a variable light ($V_L$) chain substantially similar to SEQ ID NO:4. In some embodiments, the anti-CD22 antibody will be an anti-CD22 Fv fragment; preferably a dsFv fragment.

In addition the kits will typically include instructional materials disclosing means of use of an antibody of the present invention (e.g. for detection of B cells in a sample). The kits may also include additional components to facilitate the particular application for which the kit is designed. Thus, for example, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

Detectable Labels

Antibodies of the present invention may optionally be covalently or non-covalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, texas red, rhodamine, green fluorescent protein, and the like), radiolabels (e.g., 3H, 125I, 35S, 14C, or 32P), enzymes (e.g., horse radish peroxidase, alkaline phosphatase and others commonly used in an ELISA), and calorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and calorimetric labels are detected by simply visualizing the colored label.

Other Therapeutic Moieties

Antibodies of the present invention can also be used to target any number of different diagnostic or therapeutic compounds to cells bearing CD22 antigens. Thus, an antibody of the present invention, such as an anti-CD22 Fv fragment, may be attached directly or via a linker to a drug that is to be delivered directly to cells bearing CD22. Therapeutic agents include such compounds as nucleic acids, proteins, peptides, amino acids or derivatives, glycoproteins, radioisotopes, lipids, carbohydrates, or recombinant viruses. Nucleic acids therapeutic and diagnostic moieties include anti-sense nucleic acids, derivatized oligonucleotides for covalent cross-linking with single or duplex DNA, and triplex forming oligonucleotides.

Alternatively, the molecule bound to an anti-CD22 antibody may be an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735, Connor et al., *Pharm. Ther.*, 28: 341-365 (1985).

Conjugation to the Antibody

Therapeutic, diagnostic, or encapsulation molecules or systems can be linked to the anti-CD22 antibodies or immunoconjugates of the present invention using any number of means known to those of skill in the art. Both covalent and noncovalent attachment means may be used with anti-CD22 antibodies of the present invention.

The procedure for attaching an agent to an antibody or other polypeptide targeting molecule will vary according to the chemical structure of the agent. Polypeptides typically contain variety of functional groups; e.g., carboxylic acid (COOH) or free amine (—NH2) groups, which are available for reaction with a suitable functional group on an effector molecule to bind the effector thereto.

Alternatively, the targeting molecule and/or effector molecule may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form the desired immunoconjugate. Alternatively, derivatization may involve chemical treatment of the targeting molecule, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659,839). Many procedure and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. *Cancer Res.* 47: 4071-4075 (1987)).

In some circumstances, it is desirable to free the effector molecule from the targeting molecule when the chimeric molecule has reached its target site. Therefore, chimeric conjugates comprising linkages which are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

CD22 Protein Immunoassays

Means of detecting CD22 proteins of the present invention (i.e., CD22 and RFB4 immunoreactive fragments thereof) are not critical aspects of the present invention. The CD22 proteins can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume 37: Antibodies in Cell Biology*, Asai, ed. Academic Press, Inc. New York (1993); *Basic and Clinical Immunology* 7th Edition, Stites & Terr, eds. (1991). Immunological binding assays (or immunoassays) typically utilize an antibody to specifically bind to and often immobilize the analyte (in this case CD22 protein). The antibody employed in immunoassays of the present invention are discussed in greater detail supra. The anti-CD22 antibody may be produced by any of a number of means known to those of skill in the art as described herein.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled CD22 protein or a labeled anti-CD22 protein antibody. Alternatively, the labeling agent may be a third moiety, such as another antibody, that specifically binds to the antibody/CD22 protein complex.

In some embodiments, the labeling agent is a second CD22 protein antibody bearing a label. Alternatively, the second CD22 protein antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401-1406, and Akerstrom, et al. (1985) *J. Immunol.*, 135: 2589-2542).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting a CD22 protein in a biological sample generally comprises the steps of contacting the biological sample with an antibody which specifically reacts, under immunologically reactive conditions, to the CD22 protein. The antibody is allowed to bind to the CD22 protein under immunologically reactive conditions, and the presence of the bound antibody is detected directly or indirectly.

Although the present invention has been described in some detail by way of illustration and example for purposes of clarity of understanding, it will be obvious that certain changes and modifications may be practiced within the scope of the appended claims.

EXAMPLE 1

Example 1 describes the cloning, expression, and purification of recombinant clones expressing RFB4(scFv)PE38, RFB4 $V_H$-PE38, and RFB4 $V_L$.

Cloning

Purified RFB4 IgG was reduced with 10 mM DTT and light and heavy chains were separated on 4-20% SDS-PAGE (Novex) and blotted onto a PVDF membrane. Light and heavy chain bands were cut from the membrane and subjected to N-terminal sequence analysis. N-terminal amino acid analysis yielded sequence data for both the light and heavy chains of the RFB4 mAb which is provided in FIG. 1.

To obtain cDNAs encoding the heavy and light chain variable regions of RFB4, total RNA was prepared from RFB4 hybridoma cells and reverse transcribed to yield first strand cDNA. Subsequently PCR was performed to amplify the heavy and the light chains. Heavy and light chain specific primers were synthesized based on the N-terminal amino acid data and amplification was performed using these primers together with primers from the constant regions CH1 (heavy) and C-κ (light). This resulted in the amplification of the variable portion of the heavy chain plus part of CH1 and amplification of the variable region of the light chain plus part of C-r. PCR amplification was performed as described in Benhar I. and Pastan I. (1994), *Protein Eng.* 7, 1509-1515, except total RNA and RFB4-specific 5' primers RFB4 $V_H$5 and RFB4 $V_L$5 were used which were designed from N-terminal protein sequence data. The sequences of all primers used in cloning are listed in Table I. Primers are given 5' to 3'. Primers γCH1 and C-κ were designed as described (Benhar and Pastan, 1994). RFB4 $V_H$5 and RFB4 $V_L$5 were designed according to the N-terminal protein sequences determined by Edman degradation. RFB4 $V_H$5 encodes an NdeI site (bold) and an initiator Met (bold italicized). RFB4 $V_L$3 encodes a HindIII site (italicized). Primers RFB4 $V_H$3 and RFB4 $V_L$3 were designed according to the nucleotide sequence determined from cDNA clones. Primers RFB4 $V_H$3 and RFB4 $V_L$5 include partial Gly4Ser linker sequences which partially overlap (underlined italicized). Primer RFB4 $V_L$3 dsFv mutates $V_L$ Gly$_{100}$ residue to Cys (underlined), includes a terminator codon (bold) and an EcoRI site (italicized). Primer RFB4 $V_H$ dsFv(cys) mutates $V_H$ Arg44 to Cys (underlined). RFB4 $V_H$3 dsFv includes an additional Lys codon and a HindIII site (italicized). RFB4 $V_L$5 dsFv includes an NdeI site (bold) and an initiator Met (bold italicized).

TABLE 1

Table I. PCR primers

Heavy chain primers

| | |
|---|---|
| RFB4 VH5 | GGACCTCATATGGAAGTGCAGCTGGTGGAGTCT (SEQ ID NO:6) through (SEQ ID NO:10) |
| γCH1. | AGCAGATCCAGGGGCCAGTGGATA (SEQ ID NO:6) through (SEQ ID NO:10) |
| RFB4 VH3 | AGATCCGCCACCACCGGATCCGCCTCCGCCTGCAGAGACAGTGACCAGAGTCCC (SEQ ID NO:6) through (SEQ ID NO:10) |
| RFB4 VH3 dsFv | CCGGAAGCTTTTGCAGAGACAGTGACC (SEQ ID NO:6) through (SEQ ID NO: 10) |
| RFB4 VH dsFv(cys) | GACCCACTCCAGGCACTTCTCCGGAGTC (SEQ ID NO:6) through (SEQ ID NO:10) |

Light chain primers

| | |
|---|---|
| RFB4 VL5 | GGTGGCGGATCTGGAGGTGGCGGAAGCGATATCCAGATGACACAGACT (SEQ ID NO:11) through (SEQ ID NO:15) |
| C-κ | TGGTGGGAAGATGGATACAGTTGG (SEQ ID NO:11) through (SEQ ID NO:15) |
| RFB4 VL3 | CCGGAAGCTTTGATTTCCAGCTTGG (SEQ ID NO:11) through (SEQ ID NO:15) |
| RFB4 VL5 dsFv | GGACCTCATATGGATATCCAGATGACCC (SEQ ID NO:11) through (SEQ ID NO:15) |
| RFB4 VL3 dsFv | CCGGAATTCATTATTTGATTTCCAGCTTGGTGCCGCAACCGAACGTCC (SEQ ID NO:11) through (SEQ ID NO:15) |

Primers are given 5' to 3'. Primers γCH1 and C-κ were designed as described (Benhar and Pastan, 1994). RFB4 VH5 and RFB4 VL5 were designed according to the N-terminal protein sequences determined by Edman degradation. RFB4 VH5 encodes an NdeI site (bold) and an initiator Met (bold italicized). RFB4 VL3 encodes a HindIII site (italicized). Primers RFB4 VH3 and RFB4 VL3 were designed according to the nucleotide sequence determined from cDNA clones. Primers RFB4 VH3 and RFB4 VL5 include partial Gly$_4$Ser linker sequences which partially overlap (underlined italicized). Primer RFB4 VL3 dsFv mutates $V_L$ Gly$_{100}$ residue to Cys (underlined), includes a terminator codon (bold) and an EcoRI site (italicized). Primer RFB4 VH dsFv(cys) mutates $V_H$ Arg$_{44}$ to Cys (underlined). RFB4 VH3 dsFv includes an additional Lys codon and a HindIII site (italicized). RFB4 VL5 dsFv includes and NdeI site (bold) and an initiator Met (bold italicized).

PCR products were cloned into the PCR cloning vector (Invitrogen) and sequenced using Sequenase (US Biochemical Corp.) reagents and protocols. The nucleotide and deduced amino acid sequences of $V_H$ and $V_L$ are shown in FIG. 1.

Figure 2A:
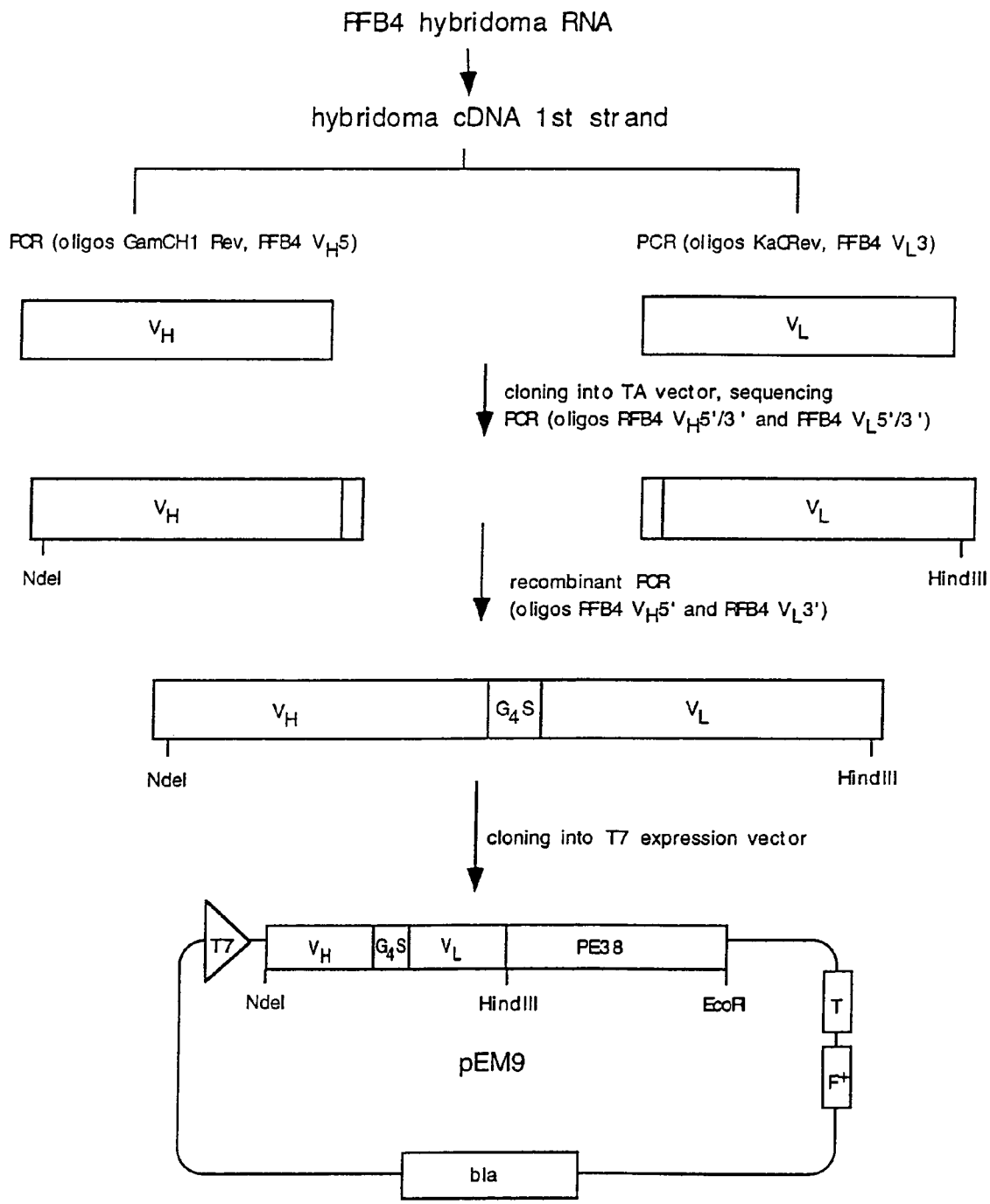
FIG. 2A: Construction of the plasmid (pEM9) encoding a single chain immunotoxin composed of the variable light and heavy chains of RFB4 fused to PE38.

$V_H$ and $V_L$ were reamplified using RFB4 $V_H$5 and RFB4 $V_L$5 primers and new RFB4-specific primers, RFB4 $V_H$3 and RFB4 $V_L$3, based on the 3' DNA sequence. $V_H$3 and $V_L$3 were designed to anneal at the 3' end of each cDNA. $V_H$3 and $V_L$5 contain overlapping sequences which encode a (Gly4Ser)$_3$ flexible peptide linker which is used to join the $V_H$ and $V_L$ chains (FIG. 2A). Recombinant PCR was performed using the amplified light and heavy chains to create a $V_H$-linker-$V_L$ product which was then used to replace the $V_H$-linker-$V_L$ of the plasmid pULI7 at the NdeI and HindIII sites, creating pEM9. This encodes the RFB4 $V_H$-linker$V_L$-PE38 fusion construct called RFB4(scFv)PE38 (FIG. 2A).

Figure 2B:
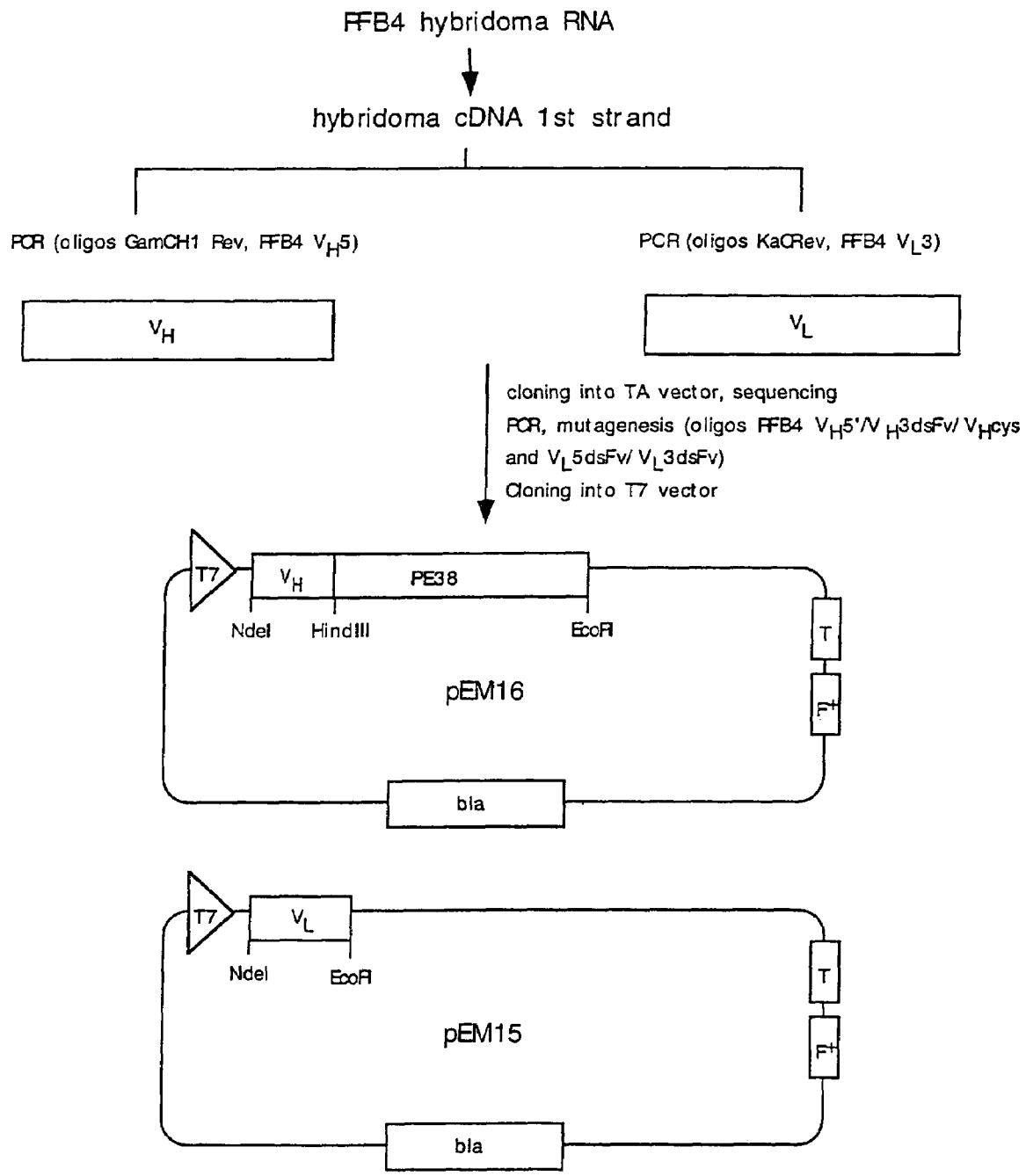
FIG. 2B: Construction of the plasmids pEM15 and pEM16 encoding the RFB4 variable light chain-cys100, and the variable heavy chain-cys$_{44}$ fused to PE38.

The binding portion of disulfide-linked immunoconjugates consists of $V_H$ and $V_L$ chains that are covalently linked through a single key residue in each chain that has been mutated to cysteine. The cysteine residues of each chain associate to form a disulfide bond which is generally very stable and markedly decreases the tendency of the immunotoxin to aggregate. Reiter et al., (1994), *Biochemistry* 33, 5451-9. To make RFB4(dsFv)PE38, $V_L$ was amplified using a 5' primer, RFB4 dsFv, introducing an NdeI site, and a 3' primer, RFB4 $V_L$3 dsFv introducing a termination codon, an EcoRI site, and mutating glycine residue 100 to cysteine. $V_H$ was amplified using RFB4 $V_H$5 and RFB4 $V_H$3 dsFv which introduces a HindIII site and a lysine residue at the C-terminus of $V_H$. PCR products were digested with NdeI and either HindIII ($V_H$) or EcoRI ($V_L$) and were used to replace $V_H$-linker-$V_L$ of pULI7 ($V_H$) or to replace the entire $V_H$-linker-$V_L$-PE38 ($V_L$). The cloned product pEM16 (encoding RFB4 $V_L$-Cys$_{100}$) was sequenced and shown to have incorporated the Gly to Cys mutation (FIG. 2B). $V_H$-PE38 was mutagenized to change Arg44 to Cys using the Muta-Gene site-directed mutagenesis kit and protocol (Bio-Rad) and a phosphorylated primer, $V_H$dsFv(cys). The resulting mutated construct, pEM15, was sequenced and shown to have incorporated the Arg to Cys mutation (FIG. 2B). Clones that had incorporated the Cys44 mutation were identified by DNA sequencing (FIG. 2B).

Expression and Purification of Recombinant Clones

Expression plasmids encoding RFB4(scFv)PE38, RFB4 $V_H$-PE38 and RFB4 $V_L$ (i.e., pEM10, and pEM15 and pEM16) were separately expressed in *E. coli* BL21(λDE3). Studier F. W. and Moffatt B. A. (1986), *J. Mol. Biol.* 189, 113-130. Cultures of transformed bacteria were induced with IPTG for high level expression, with the protein products accumulating in inclusion bodies. Single chain and disulfide-linked immunotoxins were produced by refolding of purified inclusion body protein generally as described. Buchner J., Pastan I. and Brinkmann U. (1992), *Anal. Biochem.* 205, 263-270. Briefly, inclusion bodies were prepared from cell paste by lysis and washing in non-ionic detergent, then solubilized in 6 M guanidine-HCl, 0.1 M Tris, pH 8.2 mM EDTA. Solubilized protein at 10 mg/ml was reduced with 10 mg/ml DTE (65 mM), then rapidly diluted into 100 vol. 0.1 M Tris, 0.5 M L-arginine, 0.9 mM oxidized glutathione, 2 mM EDTA at 10° C. Equal weight amounts of $V_L$ and PE38 were used to refold RFB4(dsFv)PE38. Single chain immunotoxin was refolded in buffer adjusted to pH 8 (room temperature) and dsFv was refolded in buffer adjusted to pH 9.5 (room temperature). Immunotoxins were allowed to refold for 48 hours, then were dialyzed against 100 mM urea, 20 mM Tris, pH 8 to a conductivity of less than 3.5 mMho. Properly refolded proteins were purified by sequential anion-exchange FPLC on Q-Sepharose and MonoQ (Pharmacia, Arlington Heights, Ill.) followed by gel filtration on 30 ml TSK G3000SW (Toso-Haas, Montgomeryville, Pa.). Purified immunotoxins were stored at –80° C.

EXAMPLE 2

Example 2 describes a binding assay to study the relative binding affinities of recombinant immunotoxins.

Figure 4:
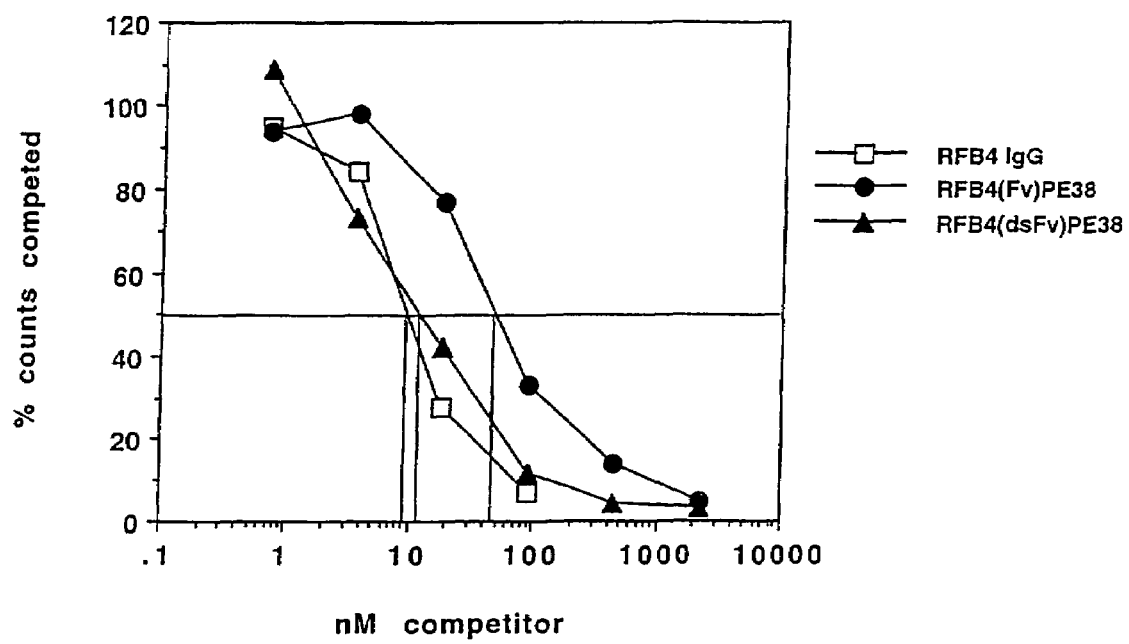
FIG. 4: The relative binding activity of RFB4 immunotoxins compared to native antibody on CA46 cells. Whole antibody and recombinant immunotoxins were used to compete for binding of trace amounts of $^{125}$I-labeled RFB4 IgG. Counts competed are expressed as a percentage of counts from cells that were incubated without any competitor. Open squares RFB4 IgG; closed circles RFB4(scFv)PE38; closed triangles RFB4(dsFv)PE38.

Relative binding affinities of recombinant immunotoxins was measured by competition against $^{125}$I-labelled RFB4 IgG for binding to CA46 target cells at 4° C. CA46 cells grown to >10$^6$/ml were washed twice in ice cold binding buffer (RPMI, 50 mM BES, pH 6.8, 1% BSA), and plated at 10$^6$ cells/150 μl binding buffer/well in 96-well plates on ice. To the cells was added 0.35 ng $^{125}$I-RFB4 (2.5×10$^9$ cpm/nmol) in binding buffer, and varying concentrations of RFB4(Fv)PE38 and RFB4(dsFv)PE38. Cells were incubated for 3 hours on ice, washed twice in cold binding buffer, and solubilized in 200 μl 0.5% SDS/TE. Bound $^{125}$I-RFB4 was quantitated on a Wallac 1470 Wizard gamma counter. The means of duplicate samples were used for calculations. As shown in FIG. 4, a 50% reduction in binding of $^{125}$I-RFB4 IgG to CA46 cells was achieved at 70 nM RFB4(scFv)PE38 and to Daudi at 90 nM RFB4(scFv)PE38. Binding to CA46 cells was reduced by 50% at 10 nM RFB4(dsFv)PE38. Native RFB4 IgG reduced the binding of labelled RFB4 IgG to CA46 cells by 50% at 4.5 nM and to Daudi cells at 10 nM.

EXAMPLE 3

Example 3 describes a stability study of RFB4(dsFv)PE38 and RFR4(scFv)PE38 for extended periods at 37° C.

Figure 5:
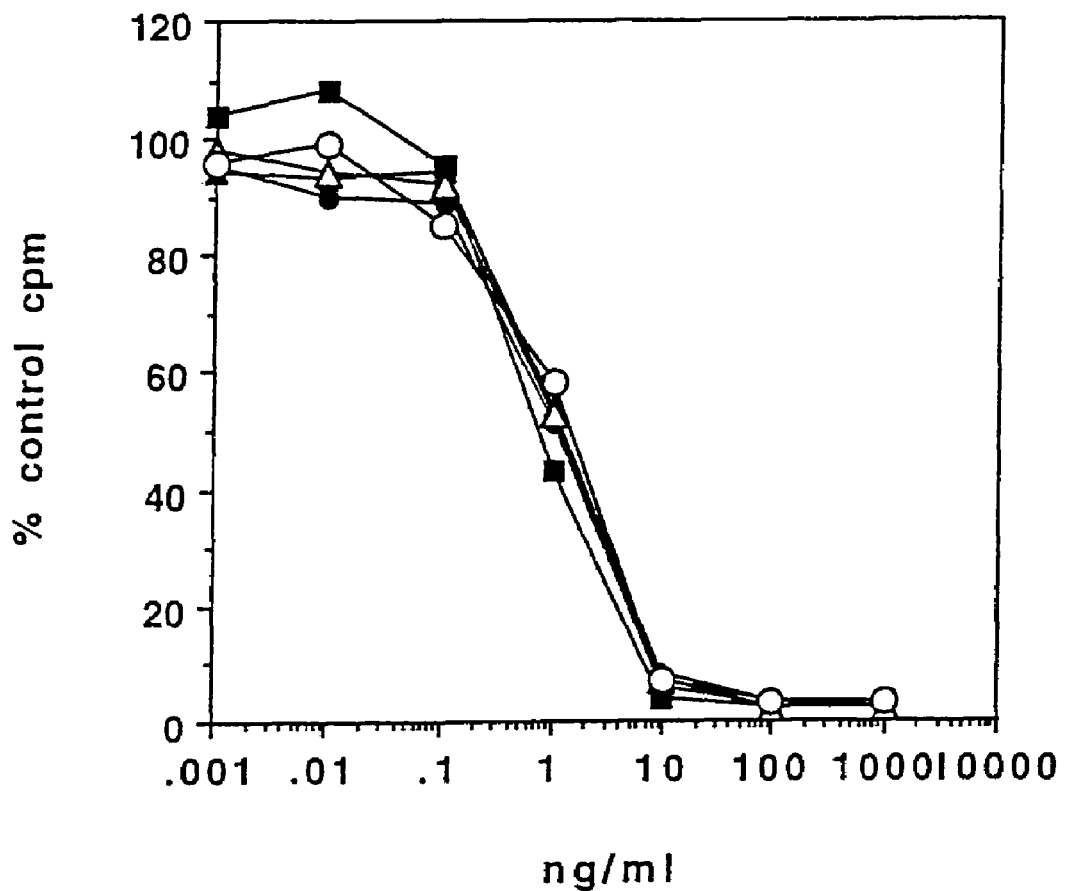
FIG. 5: Stability of RFB4(dsFv)PE38. RFB4(dsFv)PE38 was incubated at 37° C. for the number of days indicated and cytotoxicity was compared to a sample that was not incubated at 37° C. Open circles 7 days; open triangles 5 days; closed circles 3 days; closed triangles 1 day; closed squares 0 days.

Stability of PE-based recombinant immunotoxins has been correlated with their activity in vitro. Benhar I. and Pastan I. (1994), *Protein Eng.* 7, 1509-1515. Accordingly, RFB4 (dsFv)PE38 was incubated at 37° C. for 1-7 days and its cytotoxic activity after incubation was compared to that of untreated immunotoxin. RFB4(Fv)PE38 was incubated for 2-24 hours at 37° C. The cytotoxicities of the treated samples were compared to samples which were kept at −80° C. In keeping with the previous finding of high stability of dsFv immunotoxins at 37° C., RFB4(dsFv)PE38 was also very stable over the entire 7 days as judged by maintenance of full cytotoxic activity in a 24 hour assay (FIG. 5). In similar assays, RFB4(Fv)PE38 lost no cytotoxicity after 24 hour incubation at 37° C.

EXAMPLE 4

Example 4 describes cytotoxicity assays using a variety of cell types.

Figure 3:
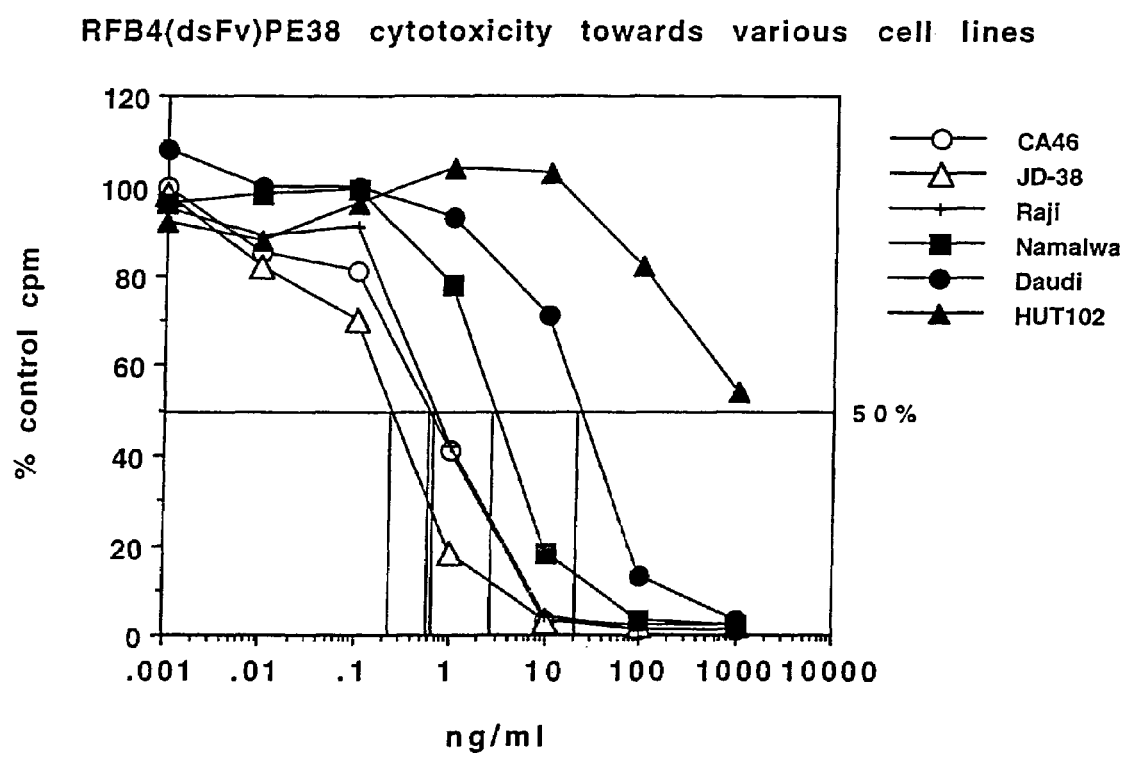
FIG. 3: Cytotoxicity of RFB4(dsFv)PE38 for various cell lines after 24 hour incubation. [$^3$H]leucine incorporation is expressed as a percentage of cpm incorporated by control cells incubated without immunotoxin. Open circles CA46; open triangles, JD-38; crosses Raji; closed squares Namalwa; closed circles Daudi; closed triangles HUT102.

RFB4(scFv)PE38 and RFB4(dsFv)PE38 (FIG. 3) were tested on five Burkitt's lymphoma cell lines (CA46, Daudi, JD38, Namalwa, and Raji) and HUT 102, a T-cell line that is CD22-negative. Daudi, Raji, and Namalwa cells were purchased from ATCC, Rockville, Md. Cells were maintained in RPMI 1640 containing 20% (Daudi) or 10% fetal bovine serum (FBS) (all other lines), 50 U/ml penicillin, 50 μg/ml streptomycin, 1 mM sodium pyruvate and an additional 2 mM L-glutamine. For cytotoxicity assays, 4×10$^4$ cells/well in 200 μl culture medium were plated in 96-well plates. Immunotoxins were serially diluted in PBS/0.2% HSA and 10 μl added to cells. Plates were incubated for the indicated times at 37° C., then pulsed with 1 μCi/well 3$^H$-leucine in 10 μl PBS for 4-5 hours at 37° C. Radiolabeled material was captured on filtermats and counted in a Betaplate scintillation counter (Pharmacia, Gaithersburg, Md.). Triplicate sample values were averaged and inhibition of protein synthesis determined by calculating percent incorporation compared to control wells without added toxin.

RFB4(dsFv)PE38 was generally 2-7-fold more cytotoxic than RFB4(scFv)PE38 towards the Burkitt's lines, and neither had significant cytotoxic activity towards the non-B-cell lines (Table II).

TABLE II

Cytotoxicity of RFB4(scFv)PE38 and RFB4(dsFv)PE38 towards various cell lines

| Cell line$^a$ | Source | Cytotoxicity IC$_{50}$ (ng/ml)$^b$ | |
|---|---|---|---|
| | | RFB4(scFv)PE38 | RFB4(dsFv)PE38 |
| CA46 | Burkitt's lymphoma | 2 | 0.6 |
| Daudi | | 30 | 20 |
| JD-38 | | 2 | 0.3 |
| Namalwa | | 2 | 1.5 |
| Raji | | 2.5 | 0.4 |
| HUT102 | T-cell leukemia | >1000 | >1000 |

$^a$All the cell lines are of human origin.
$^b$Cytotoxicity data are given as IC$_{50}$'s, which are the concentrations of immunotoxin that cause a 50% reduction in protein synthesis compared to controls after incubation with cells for 24 hours.

Of the B-cell lines tested, there were variations in sensitivity to both RFB4 immunotoxins, with RFB4(dsFv)PE38 having an IC$_{50}$ value ranging from 0.25-0.6 ng/ml on CA46, JD38 and Raji, 1.5 ng/ml on Namalwa and 20 ng/ml on Daudi (Table II). Subsequent studies have shown that Daudi cells cannot efficiently process FE38. The cytotoxic activity of the RFB4(dsFv)PE38 immunotoxin compares favorably on a molar basis with the RFB4-PE35 immunotoxin that was constructed by joining PE35 to the RFB4 antibody via a disulfide linkage.

EXAMPLE 5

Example 5 describes the temporal measurement of cytotoxic activity of RFB4(dsFv)PE38.

The time required for cells to internalize and process immunotoxin is of therapeutic interest, because blood levels of immunotoxin in treated patients must remain above a cytotoxic threshold for long enough to intoxicate the malignant cells. Therefore, the time requirement for cytotoxicity was studied.

RFB4(dsFv)PE38 dilutions were incubated with CA46 and JD38 cells for 2, 24 and 48 hours in standard cytotoxicity assays, except that for the 2 hour time point, immunotoxin was removed from the medium by washing with RPME+10% FCS, and replaced with standard medium for the remaining 22 hours of the assay. For 48 hour assays, the cells were incubated continuously for 48 instead of 24 hours.

The 2 hour exposure was followed by 22 additional hours of incubation in immunotoxin-free medium in order to allow time for the intracellular trafficking that is required for intoxication. For both CA46 and JD38 cells, increasing the exposure time to immunotoxin from 2 to 24 hours decreased the IC$_{50}$ by 5-10-fold. Incubation of cells for 48 hours continuously with RFB4(dsFv)PE38 resulted in little if any additional effect on cytotoxicity over that observed after 24 hours of incubation. Therefore, it was concluded that the cell lines used require greater than 2 hours of exposure to bind and internalize maximal amounts of immunotoxin, and are intoxicated to nearly the fullest extent possible by 24 hours.

Increasing exposure to times greater than 24 hours does not provide any advantage in vitro.

EXAMPLE 6

Example 6 describes a toxicity study of RBF4(dsFv)PE38 and RBF4(Fv)PE38 in mice and their inhibition of CA46 tumor establishment.

Figure 6A:
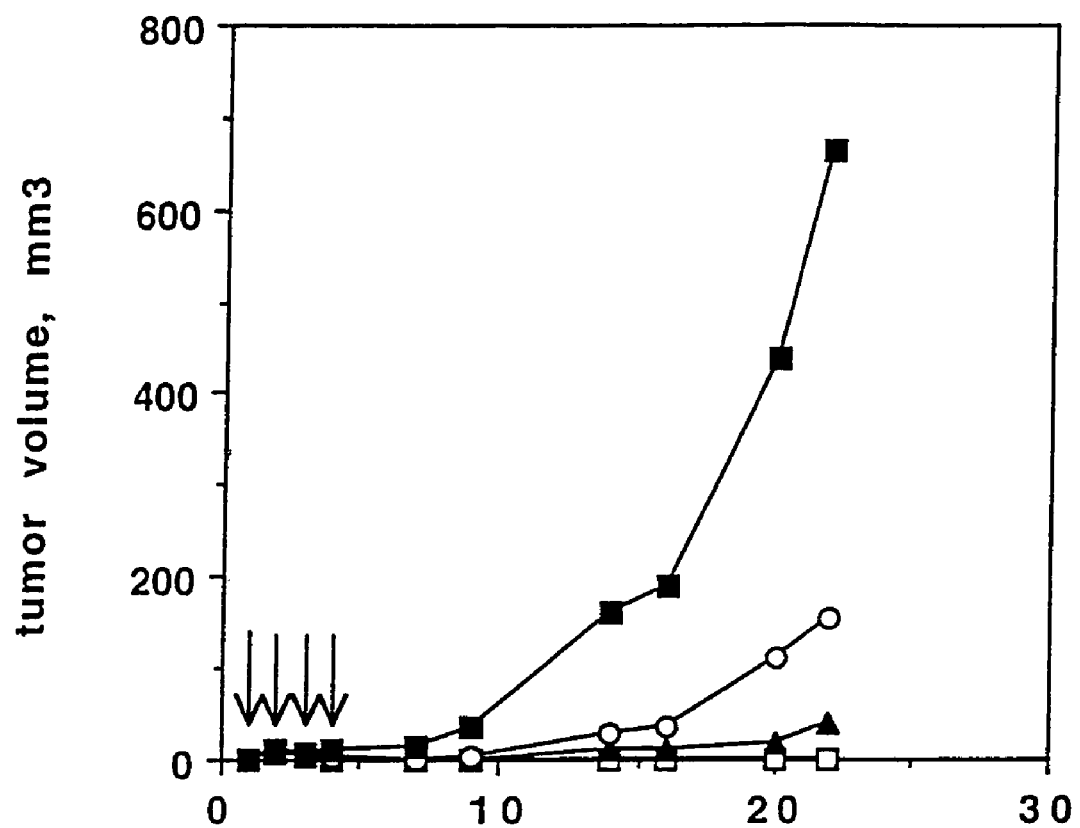
FIG. 6A: Anti-tumor-take activity of RFB4(dsFv)PE38. Athymic nude mice irradiated on day-4 were inoculated with 5×10$^6$ CA46 cells on day 0. Beginning on day 1, injections of 5, 3 or 1 μg RFB4(dsFv)PE38 or PBS/0.2% BSA diluent were given every day for four doses. Tumor growth was monitored by measuring tumor volume and is expressed as the average tumor volume of each group. Open squares 5 μg; closed triangles 3 μg; open circles 1 μg; closed squares PBS/0.2% BSA diluent control.
Figure 6B:
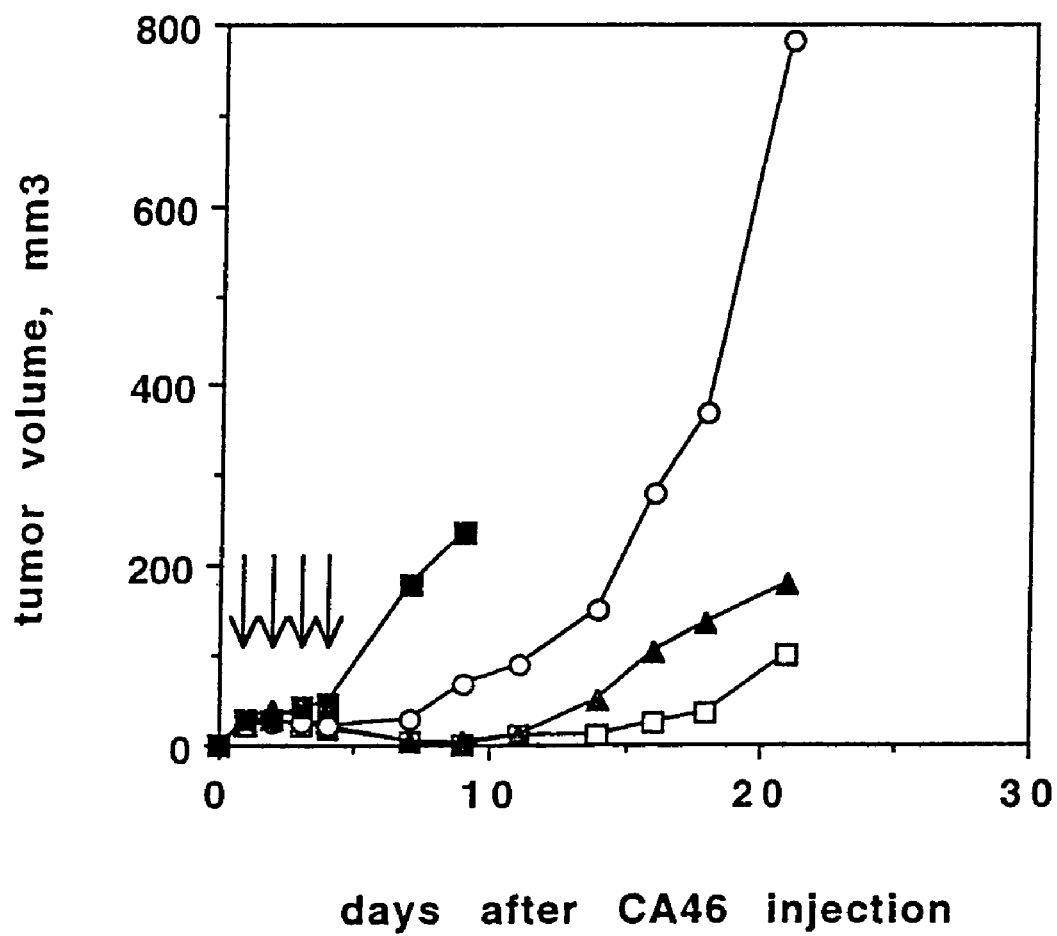
FIG. 6B: Anti-tumor-take activity of RFB4(dsFv)PE38. Athymic nude mice irradiated on day-3 were inoculated with 10$^7$ CA46 cells on day 0. Beginning on day 1, injections of 5, 2 or 1 μg RFB4(dsFv)PE38 or PBS/0.2% BSA were given every day for four doses. Tumor growth was monitored by measuring tumor volume and is expressed as the average tumor volume of each group. Open squares 5 μg; closed triangles 2 μg; open circles 1 μg; closed squares PBS/0.2% BSA diluent control.

The excellent cytotoxicity and stability of RFB4(dsFv) PE38 in vitro predicted that this molecule would have good anti-tumor activity in an animal model of lymphoma. The ability of RFB4(dsFv)PE38 to inhibit tumor take in a subcutaneous solid tumor model was initially evaluated using CA46 Burkitt's lymphoma cells injected into nude mice. Two protocols were used. In the first protocol, mice were irradiated on day −4 and injected with $5 \times 10^6$ CA46 cells. Mice were divided into groups of five and treated beginning 24 hr after injection of CA46 cells for four consecutive days (days 1-4) with various amounts of immunotoxin, in addition to diluent control (FIG. 6A). In the second protocol, female athymic nude mice were irradiated on day −3 and then injected subcutaneously with $10^7$ CA46 cells on day 0 (FIG. 6B). Tumor volumes were recorded for 21 days, and mice that did not develop tumors were monitored for an additional 80 days.

Toxicity in Mice

An initial study was performed to determine the toxicity of the immunotoxins in mice. 6-8 week old Balb/C female mice were obtained from the National Cancer Institute, Frederick, Md. Multiple-dose i.v. $LD_{50}$ values were determined for a treatment schedule of dose×3 qod. Various amounts of immunotoxins were diluted to 200 μl with PBS/0.2% HSA and injected into the tail veins every other day for 3 doses. Two mice were injected with each dose, and mice were monitored for weight loss and death for 14 days after last injection.

Inhibition of CA46 Tumor Establishment 6-8 week old female athymic nude mice were obtained from the National Cancer Institute, Frederick, Md. Mice were treated with 300 rad of gamma irradiation 3 or 4 days prior to injection of malignant cells. CA46 cells were seeded at $1.8 \times 10^5$/ml 2 days prior to injection. On day 0, CA46 cells were washed in RPMI without serum and adjusted to either $10^8$ cells/ml or $5 \times 10^6$ cells/ml in RPMI. Each mouse was given 100 μl of the cell suspension by subcutaneous injection. Mice were treated by tail vein injection every day for 4 consecutive days with various amounts of immunotoxins or with control materials in 200 μl volume. The appearance of tumors was monitored daily or every other day for 21 days following first treatment. Mice that had not grown any detectable tumor after 21 days were monitored for up to 100 days for the growth of tumors at the injection site. Mice inoculated using the second protocol and treated with 5 or 3 μg of RFB4(dsFv)PE38 developed very small tumor nodules that completely regressed upon treatment in all mice at the 5 μg dose and in 9 of 10 mice at the 3 μg dose. Treatment with 1 μg of immunotoxin delayed tumor development significantly throughout the observation period but did not produce cures.

Immunotoxin Activity Against Established CA46 Tumors

The success of anti-tumor experiments (above) encouraged an examination of the ability of RFB4(dsFv)PE38 to eradicate established tumors. Athymic female nude niece were irradiated on day −3 and then injected with $10^7$ CA46 cells on day 0. By day 4, the majority of mice had grown tumors that were 5×5 mm in size. Starting on day 4, tumor-bearing mice were treated daily for 4 days or every other day for 3 days. Treatment was given by injection in the tail vein for 5 consecutive days with various amounts of immunotoxin or with control materials. Tumor size was monitored daily or every other day using precision calipers. Tumor volume was calculated by the formula $v=l(w^2) \times 0.4$ where l is length and w is width.

Figure 7A:
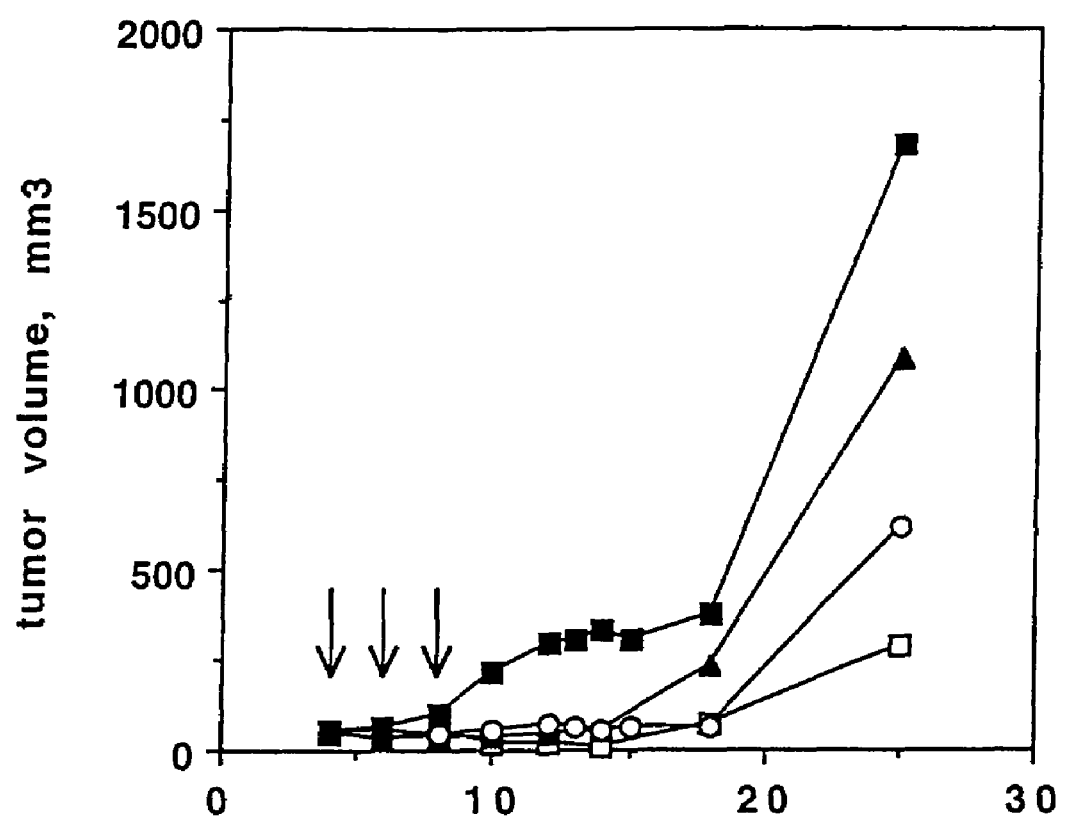
FIG. 7A: Antitumor activity of RFB4(dsFv)PE38 against CA46 tumors. Athymic nude mice were irradiated on day-3 and inoculated with 10$^7$ CA46 cells on day 0. Beginning on day 4, mice with tumor sizes averaging 50 mm$^3$ were treated with 8, 5 or 3 μg RFB4(dsFv)PE38 or with PBS/0.2% BSA diluent every other day for three doses. Tumor size was monitored by measuring tumor volume, and is expressed as the average tumor volume of each group. 3/5 mice receiving 8 μg of RFB4(dsFv)PE38 died during treatment, and 1/5 receiving 5 μg died. Open squares 8 μg; closed triangles 5 μg; open circles 3 μg; closed squares PBS/0.2% BSA diluent control.
Figure 7B:
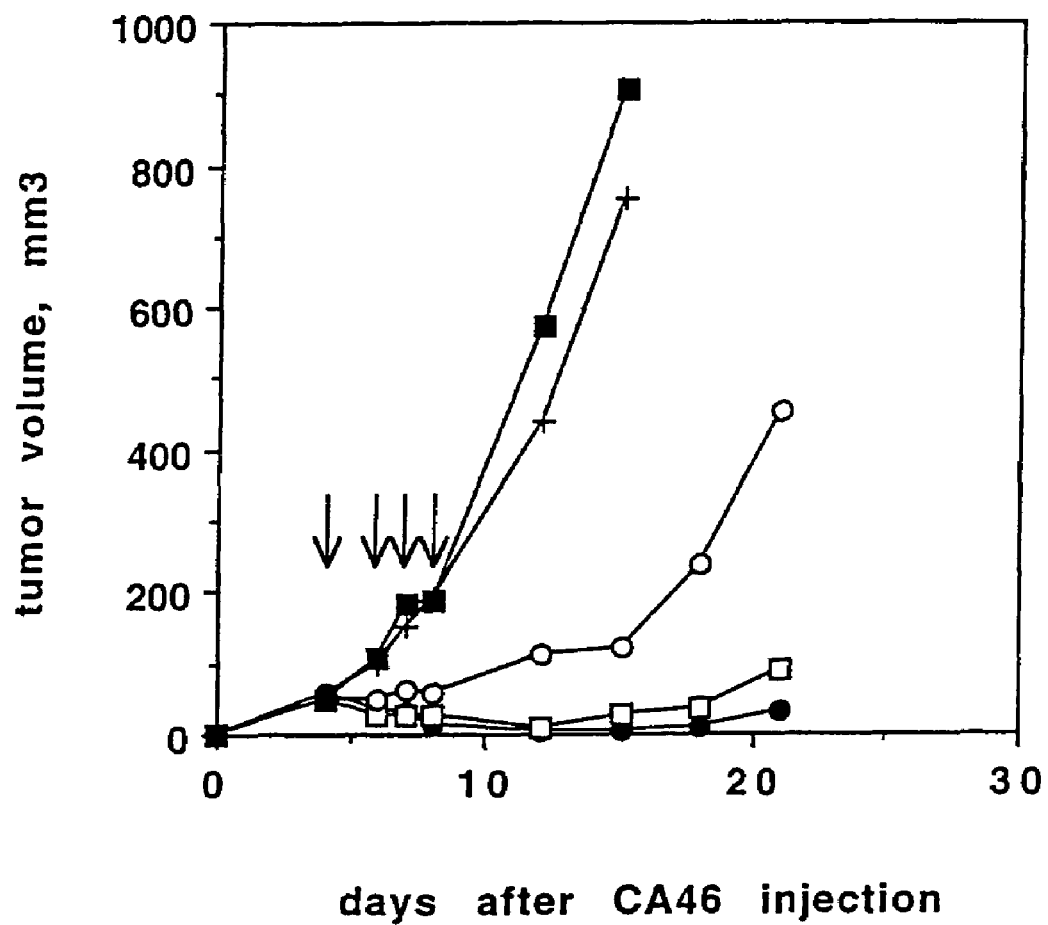
FIG. 7B: Antitumor activity of RFB4(dsFv)PE38 against CA46 tumors. Athymic nude mice were irradiated on day −3 and inoculated with 107 CA46 cells on day 0. Beginning on day 4, mice with tumor sizes averaging 50 mm$^3$ were treated with 8, 5 or 1 μg RFB4(dsFv)PE38 or with 30 μg RFB4 IgG or with PBS/0.2% BSA diluent on days 4, 6, 7 and 8. Tumor size was monitored by measuring tumor volume, and is expressed as the average tumor volume of each group. 3/5 mice receiving 8 μg of RFB4(dsFv)PE38 died-during treatment, and 2/5 receiving 5 μg died. Closed circles 8 μg; open squares 5 μg; open circles 1 μg; crosses 30 μg RFB4 IgG; closed squares PBS/0.2% BSA diluent control.
Figures 8A, 8B:
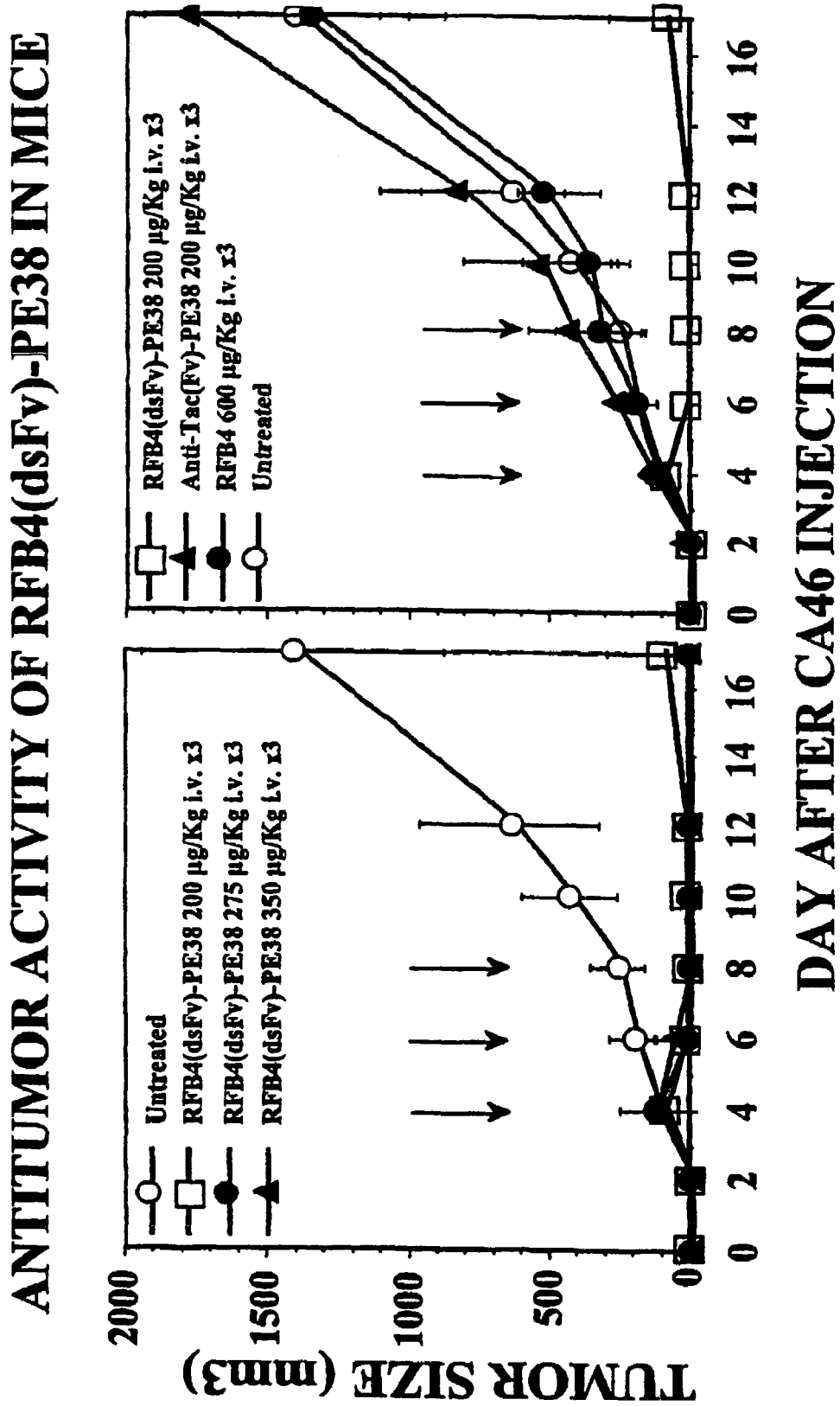
FIGS. 8A and 8B: Antitumor activity of RFB4(dsFv)-PE38 in mice.

Using either treatment protocol, inhibition of tumor growth was observed with a duration of one week to 10 days following the last administration of immunotoxin (FIGS. 7A, 7B). These antitumor responses were achieved using 8, 5 or 3 μg of RFB4(dsFv)PE38. Tumors in all treated mice eventually resumed growth. Doses of 30 μg of RFB4 IgG alone did not significantly inhibit growth of tumors, while 1 μg of RFB4 (dsFv)PE38 could inhibit growth during the period of immunotoxin administration. Mice inoculated and treated with either 5 or 2 ug of immunotoxin developed small tumor cell nodules that regressed upon treatment and then slowly regrew. Treatment with 1 μg of immunotoxin delayed tumor development compared to controls but tumors grew rapidly thereafter.

In sum, the studies show that both immunotoxin molecules are stable at 37° C. for extended incubation times. Cytotoxicity profiles on several antigen-positive and antigen-negative cell lines, demonstrated that the recombinant molecules were highly and selectively toxic towards CD22-bearing cells, and were non-toxic towards CD22-negative lines. The duration of incubation required for maximum intoxication of cells was determined to be greater than two hours, but little additional benefit was noted at incubation times greater than 24 hours. The stability of RFB4 immunotoxins is therefore compatible with the time required for efficient intoxication.

RFB4(dsFv)PE38 is approximately 2-7-fold more active towards all sensitive cell lines than RFB4(scFv)PE38, although both have similar stabilities after 24 hours. Competition binding studies of these recombinant molecules, compared with the labeled whole IgG, showed a difference in ability to compete for binding, and an inferred reduced affinity of RFB4(scFv)PE38 for CD22 antigen.

Because the disulfide-linked immunotoxin was quite stable, had binding properties similar to the whole antibody, and superior cytotoxic effects, it was chosen for further evaluation in animal models. Its antitumor activity was evaluated by assessing its ability to eradicate tumors formed from the injection of CA46 cells into irradiated nude mice and showed it could eradicate tumor cells when immunotoxin administration began 24 hr after tumor implantation and had, significant anti-tumor activity when given to mice with established tumors. Compared to control-treated tumors, treatment with any amount of RFB4(dsFv)PE38 from 1-8 μg caused the tumors to regress or maintain a static volume until the end of the treatment period and for up to an additional 10 days, depending on the dose.

EXAMPLE 7

This example describes the cytotoxicity of RFB4(dsFv)-PE38 to CD22 positive malignant cells from human patients.

Sixteen fresh samples of chronic lymphocytic leukemia cells were obtained from different human patients. Samples of hairy cell leukemia (HCL), large cell lymphoma (LCL) and prolymphocytic leukemia (PLL) were also obtained. These cells were each incubated with RFB4(dsFv)-PE38 for 24 hours as described above in Exhibit 4 in a cytotoxicity assay. The $IC_{50}$(ng/mL) of RFB4(dsFv)-PE38 for each cell sample is provided in Table III below. Also provided for comparison is the number of CD22 sites/cell. It is interesting to note that even cells with relatively low numbers of CD22 sites per cell were very effectively killed by the immunotoxin. These results indicate that RFB4(dsFv)-PE38 is significantly toxic to many fresh human chronic lymphocytic leukemia cells.

TABLE III

SENSITIVITY OF FRESH HUMAN LEUKEMIA CELLS TO RFB4(dsFv)-PE38 (BL22)

| PT # | DX | $IC_{50}$ (ng/mL) RFB4(Fv)-PE38 (BL22) | CD22 SITES/CELL |
|---|---|---|---|
| 1. | CLL | 10 | 1050 |
| 2. | CLL | 360 | 1400 |
| 3. | CLL | 43 | 430 |
| 4. | CLL | 11 | 680 |
| 5. | CLL | >1000 | 380 |
| 6. | CLL | 172 | 1070 |
| 7. | CLL | >1000 | |
| 8. | CLL | 86 | 2200 |
| 9. | CLL | 27 | 350 |
| 10. | CLL | 91 | 300 |
| 11. | CLL | 74 | 1200 |
| 12. | CLL | 61 | 800 |
| 13. | CLL | 560 | 1850 |
| 14. | CLL | 16.5 | 4700 |
| 15. | CLL | 14 | 4075 |
| 16. | CLL | 4 | 5040 |
| 17. | HCL | 1.8 | |
| 18. | LCL | 274 | |
| 19. | PLL | 31 | 600 |

EXAMPLE 8

RFB4(dsFv)-PE38 displays potent antitumor activity against CD22 positive human tumors in mice.

CA46 tumors were established in mice as described above. Mice in groups of three were intravenously injected with RFB4(dsFv)-PE38. The dosage was given in μg/Kg qodx3 as set out in the following Table IV. The Complete Response (CR) Total is also set out. A preferred effective-dose apparent from this test is 275 μg/Kg i.v. qodx3.

In a toxicity assay in tumor established mice where the dosages of RFB4(dsFv)-PE38 began at 275 μg/Kg up to 1200 μg/Kg, an $LD_{10}$ was obtained at 500 μg/Kg i.v. qodx3 and an $LD_{50}$ was obtained at 900 μg/Kg i.v. qodx3. See Table V. The number of mice tested and the number of mortalities per dosage range is provided.

In a similar antitumor assay in mice as above, a test was run where the RFB4(dsFv)-PE38 was administered by continuous infusion i.p. at the dosages provided below and with the results provided below in Table VI. Thus, the drug was effective in inhibiting tumor activity in mice.

TABLE IV

Antitumor Activity of RFB4(dsFv)-PE38 in Mice treated i.v.

| Dose (μg/Kg QOD x3) | CR/total | % CR |
|---|---|---|
| 0 | 0/13 | 0 |
| 200 | 4/5 | 80 |
| 275 | 14/14 | 100 |
| 345 | 7/7 | 100 |

Minimum Effective Dose = 275 μg/Kg i.v. QOD x3

TABLE V

Toxicity of RFB4(dsFv)-PE38 in Mice treated i.v.

| Dose (μg/Kg QOD x3) | Deaths/total | % Mortality |
|---|---|---|
| 0 | 0/13 | 0 |
| 275 | 0/14 | 0 |
| 400 | 0/10 | 0 |
| 600 | 2/10 | 20 |
| 1200 | 4/5 | 80 |

$LD_{10}$ = 500 μg/Kg i.v. QOD x3
$LD_{50}$ = 900 μg/Kg i.v. QOD x3

TABLE VI

Antitumor activity and toxicity of RFB4(dsFv)-PE38 by continuous infusion i.p. in mice

| Dose | CR's | Deaths |
|---|---|---|
| 50 μg/Kg/d | 0/5 | 0/5 |
| 100 μg/Kg/d | 5/5 | 0/5 |
| 200 μg/Kg/d | 5/5 | 0/5 |
| 500 μg/Kg/d | | 4/5 |
| 1000 μg/Kg/d | | 5/5 |

Since RFB4 binds to primate but not murine CD22, toxicology studies were performed in cynomolgus monkeys, who tolerated RFB4(dsFv)-PE38 well up to 500 μg/Kg i.v. QODx 3.

EXAMPLE 9

Tolerance of Monkeys to RFB4(dsFv)-PE38.

Since RFB4 binds to primate CD22 and does not bind to murine CD22, toxicology studies were performed in Cynomolgus monkeys who tolerated RFB4(dsFv)-PE38 well up to 500 ug/Kg i.v. qodx3. The dosages administered to the monkeys were as follows:

0.1 μg/Kg i.v. QODx3

0.5 μg/Kg i.v. QODx3

1.25 mg/Kg i.v. QODx3

1.75 mg/Kg i.v. QODx3

2.0 mg/Kg i.v. QODx3

The standard laboratory values were obtained from serum samples taken at days 2, 4, 6, 8, 15 and 21 and were all in the normal range except that a two-fold or less rise in the liver enzymes, transaminases and creatinine were observed. See FIGS. 9A and 9B. Thus, RFB4(dsFv)-PE38 may be administered at high doses to a mammal in which the CD22 antigen is recognized by the RFB4 antibody. A Phase I clinical trial is planned in humans with CD22 positive malignancies.

All publications and patents mentioned in this specification are herein incorporated by reference into the specification to the same extent as if each individual publication or patent was specifically and individually indicated to be incorporated herein by reference.

What is claimed is:

1. A method for inhibiting the growth of a human hairy-cell leukemia cell that expresses a CD22 molecule on the surface of the cell, said method comprising:

contacting said human hairy-cell leukemia cell in vivo with an effective amount of a recombinant immunoconjugate comprising a *Pseudomonas* exotoxin PE38 covalently linked at its amino terminus to an RFB4 disulfide-stabilized Fv (dsFv) having a variable heavy chain ($V_H$) comprising SEQ ID NO:2 in which a Cys residue is substituted for Arg at position 44; and a variable light chain ($V_L$) comprising SEQ ID NO:4 in which a Cys residue is substituted for Gly at position 100, thereby inhibiting the growth of the human hairy-cell leukemia cell.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 369 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: CDS
      (B) LOCATION: 1..369
      (D) OTHER INFORMATION: /product= "RFB4 heavy chain"

(xi) SEQUENCE DESCRIPTION: SEQ ID NO: 1:

```
GAA GTG CAG CTG GTG GAG TCT GGG GGA GGC TTA GTG AAG CCT GGA GGG      48
Glu Val Gln Leu Val Glu Ser Gly Gly Gly Leu Val Lys Pro Gly Gly
 1               5                  10                  15

TCC CTG AAA CTC TCC TGT GCA GCC TCT GGA TTC GCT TTC AGT ATC TAT      96
Ser Leu Lys Leu Ser Cys Ala Ala Ser Gly Phe Ala Phe Ser Ile Tyr
                20                  25                  30

GAC ATG TCT TGG GTT CGC CAG ACT CCG GAG AAG AGG CTG GAG TGG GTC     144
Asp Met Ser Trp Val Arg Gln Thr Pro Glu Lys Arg Leu Glu Trp Val
            35                  40                  45

GCA TAC ATT AGT AGT GGT GGT GGT ACC ACC TAC TAT CCA GAC ACT GTG     192
Ala Tyr Ile Ser Ser Gly Gly Gly Thr Thr Tyr Tyr Pro Asp Thr Val
 50                  55                  60

AAG GGC CGA TTC ACC ATC TCC AGA GAC AAT GCC AAG AAC ACC CTG TAC     240
Lys Gly Arg Phe Thr Ile Ser Arg Asp Asn Ala Lys Asn Thr Leu Tyr
 65                  70                  75                  80

CTG CAA ATG AGC AGT CTG AAG TCT GAG GAC ACA GCC ATG TAT TAC TGT     288
Leu Gln Met Ser Ser Leu Lys Ser Glu Asp Thr Ala Met Tyr Tyr Cys
                85                  90                  95

GCA AGA CAT AGT GGC TAC GGT AGT AGC TAC GGG GTT TTG TTT GCT TAC     336
Ala Arg His Ser Gly Tyr Gly Ser Ser Tyr Gly Val Leu Phe Ala Tyr
                100                 105                 110

TGG GGC CAA GGG ACT CTG GTC ACT GTC TCT GCA                         369
Trp Gly Gln Gly Thr Leu Val Thr Val Ser Ala
            115                 120
```

(2) INFORMATION FOR SEQ ID NO: 2:

(i) SEQUENCE CHARACTERISTICS:
      (A) LENGTH: 123 amino acids
      (B) TYPE: amino acid
      (D) TOPOLOGY: linear (ii) MOLECULE TYPE: protein (xi) SEQUENCE DESCRIPTION: SEQ ID NO: 2:

```
Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Ala Phe Ser Ile Tyr
                20                  25                  30

Asp Met Ser Trp Val Arg Gln Thr Pro Glu Lys Arg Leu Glu Trp Val
            35                  40                  45

Ala Tyr Ile Ser Ser Gly Gly Gly Thr Thr Tyr Tyr Pro Asp Thr Val
```

-continued

```
                50                  55                  60
Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg His Ser Gly Tyr Gly Ser Ser Tyr Gly Val Leu Phe Ala Tyr
                100                 105                 110

Trp Gly Gln Gly Thr Leu Val Thr Val Ser Ala
            115                 120

(2) INFORMATION FOR SEQ ID NO: 3:

(i) SEQUENCE CHARACTERISTICS:
          (A) LENGTH: 321 base pairs
          (B) TYPE: nucleic acid
          (C) STRANDEDNESS: single
          (D) TOPOLOGY: linear (ii) MOLECULE TYPE: DNA (ix) FEATURE:
          (A) NAME/KEY: CDS
          (B) LOCATION: 1..321
          (D) OTHER INFORMATION: /product= "RFB4 light chain"

(xi) SEQUENCE DESCRIPTION: SEQ ID NO: 3:

GAT ATC CAG ATG ACC CAG ACT ACA TCC TCC CTG TCT GCC TCT CTG GGA      48
Asp Ile Gln Met Thr Gln Thr Thr Ser Ser Leu Ser Ala Ser Leu Gly
 1               5                  10                  15

GAC AGA GTC ACC ATT AGT TGC AGG GCA AGT CAG GAC ATT AGC AAT TAT      96
Asp Arg Val Thr Ile Ser Cys Arg Ala Ser Gln Asp Ile Ser Asn Tyr
                 20                  25                  30

TTA AAC TGG TAT CAG CAG AAA CCA GAT GGA ACT GTT AAA CTC CTG ATC     144
Leu Asn Trp Tyr Gln Gln Lys Pro Asp Gly Thr Val Lys Leu Leu Ile
             35                  40                  45

TAC TAC ACA TCA ATA TTA CAC TCA GGA GTC CCA TCA AGG TTC AGT GGC     192
Tyr Tyr Thr Ser Ile Leu His Ser Gly Val Pro Ser Arg Phe Ser Gly
 50                  55                  60

AGT GGG TCT GGA ACA GAT TAT TCT CTC ACC ATT AGC AAC CTG GAG CAA     240
Ser Gly Ser Gly Thr Asp Tyr Ser Leu Thr Ile Ser Asn Leu Glu Gln
 65                  70                  75                  80

GAA GAT TTT GCC ACT TAC TTT TGC CAA CAG GGT AAT ACG CTT CCG TGG     288
Glu Asp Phe Ala Thr Tyr Phe Cys Gln Gln Gly Asn Thr Leu Pro Trp
                 85                  90                  95

ACG TTC GGT GGA GGC ACC AAG CTG GAA ATC AAA                         321
Thr Phe Gly Gly Gly Thr Lys Leu Glu Ile Lys
                100                 105

(2) INFORMATION FOR SEQ ID NO: 4:

(i) SEQUENCE CHARACTERISTICS:
          (A) LENGTH: 107 amino acids
          (B) TYPE: amino acid
          (D) TOPOLOGY: linear (ii) MOLECULE TYPE: protein (xi) SEQUENCE DESCRIPTION: SEQ ID NO: 4:

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn Tyr
                 20                  25                  30

Leu Asn Trp Tyr Gln Gln Lys Pro Asp Gly Thr Val Lys Leu Leu Ile
```

```
                 35                  40                  45
Tyr Tyr Thr Ser Ile Leu His Ser Gly Val Pro Ser Arg Phe Ser Gly
         50                  55                  60

Ser Gly Ser Gly Thr Asp Tyr Ser Leu Thr Ile Ser Asn Leu Glu Gln
 65                  70                  75                  80

Glu Asp Phe Ala Thr Tyr Phe Cys Gln Gln Gly Asn Thr Leu Pro Trp
                 85                  90                  95

Thr Phe Gly Gly Gly Thr Lys Leu Glu Ile Lys
             100                 105
```

(2) INFORMATION FOR SEQ ID NO: 5:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

```
Gly Gly Gly Ser
 1
```

(2) INFORMATION FOR SEQ ID NO: 6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..33
        (D) OTHER INFORMATION: /note= "RFB4 VH5 heavy chain primer"

(xi) SEQUENCE DESCRIPTION: SEQ ID NO: 6:

GGACCTCATA TGGAAGTGCA GCTGGTGGAG TCT                         33

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..24
        (D) OTHER INFORMATION: /note= "gamma-CH1 heavy chain primer"

(xi) SEQUENCE DESCRIPTION: SEQ ID NO: 7:

AGCAGATCCA GGGGCCAGTG GATA                                   24

(2) INFORMATION FOR SEQ ID NO: 8:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (ix) FEATURE:
              (A) NAME/KEY: -
              (B) LOCATION: 1..54
              (D) OTHER INFORMATION: /note= "RFB4 VH3 heavy chain primer"

(xi) SEQUENCE DESCRIPTION: SEQ ID NO: 8:

AGATCCGCCA CCACCGGATC CGCCTCCGCC TGCAGAGACA GTGACCAGAG TCCC          54

(2) INFORMATION FOR SEQ ID NO: 9:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..27
              (D) OTHER INFORMATION: /note= "RFB4 VH3 dsFv heavy chain
                   primer"

(xi) SEQUENCE DESCRIPTION: SEQ ID NO: 9:

CCGGAAGCTT TTGCAGAGAC AGTGACC                                       27

(2) INFORMATION FOR SEQ ID NO: 10:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..28
              (D) OTHER INFORMATION: /note= "RFB4 VH dsFv(cys) heavy chain
                   primer"

(xi) SEQUENCE DESCRIPTION: SEQ ID NO: 10:

GACCCACTCC AGGCACTTCT CCGGAGTC                                      28

(2) INFORMATION FOR SEQ ID NO: 11:

(i) SEQUENCE CHARACTERISTICS:
              (A) LENGTH: 48 base pairs
              (B) TYPE: nucleic acid
              (C) STRANDEDNESS: single
              (D) TOPOLOGY: linear (ii) MOLECULE TYPE: DNA (ix) FEATURE:
              (A) NAME/KEY: -
              (B) LOCATION: 1..48
              (D) OTHER INFORMATION: /note= "RFB4 VL5 light chain primer"

(xi) SEQUENCE DESCRIPTION: SEQ ID NO: 11:

GGTGGCGGAT CTGGAGGTGG CGGAAGCGAT ATCCAGATGA CACAGACT                 48

(2) INFORMATION FOR SEQ ID NO: 12:

(i) SEQUENCE CHARACTERISTICS:
              (A) LENGTH: 24 base pairs
              (B) TYPE: nucleic acid

```
        (C) STRANDEDNESS: single
        (D) TOPOLOGY: linear (ii) MOLECULE TYPE: DNA (ix) FEATURE:
        (A) NAME/KEY: -
        (B) LOCATION: 1..24
        (D) OTHER INFORMATION: /note= "C-kappa light chain primer"

(xi) SEQUENCE DESCRIPTION: SEQ ID NO: 12:

TGGTGGGAAG ATGGATACAG TTGG                                              24

(2) INFORMATION FOR SEQ ID NO: 13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..25
        (D) OTHER INFORMATION: /note= "RFB4 VL3 light chain primer"

(xi) SEQUENCE DESCRIPTION: SEQ ID NO: 13:

CCGGAAGCTT TGATTTCCAG CTTGG                                             25

(2) INFORMATION FOR SEQ ID NO: 14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..28
        (D) OTHER INFORMATION: /note= "RFB4 VL5 dsFv light chain
            primer"

(xi) SEQUENCE DESCRIPTION: SEQ ID NO: 14:

GGACCTCATA TGGATATCCA GATGACCC                                          28

(2) INFORMATION FOR SEQ ID NO: 15:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..48
        (D) OTHER INFORMATION: /note= "RFB4 VL3 dsFv light chain
            primer"

(xi) SEQUENCE DESCRIPTION: SEQ ID NO: 15:

CCGGAATTCA TTATTTGATT TCCAGCTTGG TGCCGCAACC GAACGTCC                    48
```